(12) United States Patent
Hiraizumi et al.

(10) Patent No.: US 10,945,917 B2
(45) Date of Patent: Mar. 16, 2021

(54) DETECTION APPARATUS FOR DETECTING TAKING-OUT OF CONTAINED OBJECT FROM BLISTER PACK, DETECTION METHOD THEREFOR, AND MEDICATION MANAGEMENT SYSTEM

(71) Applicant: NIPPON FRONTIER MEDICINE LABORATORIES, INC., Osaka (JP)

(72) Inventors: Kazuki Hiraizumi, Yamaguchi (JP); Junichi Fukui, Osaka (JP); Kunihiro Musashi, Osaka (JP)

(73) Assignee: NIPPON FRONTIER MEDICINE LABORATORIES INC., Osaka (JP)

( * ) Notice: Subject to any disclaimer, the term of this patent is extended or adjusted under 35 U.S.C. 154(b) by 0 days.

(21) Appl. No.: 16/092,955

(22) PCT Filed: Apr. 17, 2017

(86) PCT No.: PCT/JP2017/015502
§ 371 (c)(1),
(2) Date: Oct. 11, 2018

(87) PCT Pub. No.: WO2017/179741
PCT Pub. Date: Oct. 19, 2017

(65) Prior Publication Data
US 2019/0117509 A1 Apr. 25, 2019

(30) Foreign Application Priority Data

Apr. 15, 2016 (JP) .............................. JP2016-082135
Apr. 17, 2017 (JP) .............................. JP2017-081177

(51) Int. Cl.
*G08B 5/22* (2006.01)
*G08B 25/00* (2006.01)
(Continued)

(52) U.S. Cl.
CPC .............. *A61J 1/035* (2013.01); *A61J 7/0418* (2015.05); *B65B 57/10* (2013.01); *G01B 11/00* (2013.01);
(Continued)

(58) Field of Classification Search
CPC .... A61J 1/035; A61J 2200/70; A61J 2200/30; A61J 7/0409; A61J 7/0418; G01V 8/20;
(Continued)

(56) References Cited

U.S. PATENT DOCUMENTS 5,471,050 A 11/1995 Nishimoto et al.
5,777,244 A 7/1998 Kumagai et al.
(Continued)

FOREIGN PATENT DOCUMENTS

CN 102113963 A 7/2011
CN 104302555 A 1/2015
(Continued)

OTHER PUBLICATIONS

The Decision of Grant dated Feb. 12, 2019 of Japanese Patent Application No. 2016-082135.
(Continued)

*Primary Examiner* — Tanmay K Shah
(74) *Attorney, Agent, or Firm* — Ladas & Parry LLP

(57) ABSTRACT

To readily detect the taking-out of an object contained in a blister pack, there is provided a detection apparatus for detecting a timing at which a contained object is taken out from a blister pack including a plurality of containing portions and a plate-like portion that connects the plurality of containing portions. The apparatus includes a plate on which the blister pack is arranged, a plurality of light sources that emit light beams to the plurality of containing portions of the blister pack arranged on the plate, a plurality of sensors that receive the light beams emitted from the light
(Continued)

sources, and also output electrical signals corresponding to light reception intensities, and a detector that detects the presence/absence of contained objects in the respective containing portions based on the electrical signals output from the plurality of sensors.

8 Claims, 32 Drawing Sheets

(51) Int. Cl.
*A61J 1/03* (2006.01)
*B65B 57/10* (2006.01)
*G01B 11/00* (2006.01)
*G01V 8/12* (2006.01)
*G16H 20/00* (2018.01)
*A61J 7/04* (2006.01)
*G01V 8/20* (2006.01)
*G01N 21/84* (2006.01)
*G01J 1/02* (2006.01)
*G16H 20/13* (2018.01)

(52) U.S. Cl.
CPC ............... *G01J 1/02* (2013.01); *G01N 21/84* (2013.01); *G01V 8/12* (2013.01); *G01V 8/20* (2013.01); *G16H 20/00* (2018.01); *A61J 7/0409* (2013.01); *A61J 2200/30* (2013.01); *A61J 2200/70* (2013.01); *G16H 20/13* (2018.01)

(58) Field of Classification Search
CPC .. G01V 8/12; G01N 21/84; G01J 1/02; G01B 11/00; B65B 57/10; G16H 20/13; G16H 20/00
USPC .......................................................... 340/6.1
See application file for complete search history.

(56) References Cited

U.S. PATENT DOCUMENTS

| | | | |
|---|---|---|---|
| 5,917,180 A | 6/1999 | Reimer et al. | |
| 8,960,440 B1* | 2/2015 | Kronberg | A61J 1/035 |
| | | | 206/531 |
| 2007/0046713 A1 | 3/2007 | Miyahara et al. | |
| 2009/0301925 A1 | 12/2009 | Alloro et al. | |
| 2009/0315702 A1 | 12/2009 | Cohen Alloro et al. | |
| 2011/0155602 A1 | 6/2011 | Sterry et al. | |
| 2012/0154120 A1 | 6/2012 | Alloro et al. | |
| 2013/0319902 A1* | 12/2013 | Tufi | A61J 1/035 |
| | | | 206/534 |
| 2015/0247793 A1 | 9/2015 | Wakui et al. | |
| 2016/0008229 A1* | 1/2016 | Dickie | A61J 7/04 |
| | | | 340/309.7 |

FOREIGN PATENT DOCUMENTS

| | | |
|---|---|---|
| JP | 64049940 A | 2/1989 |
| JP | 2043674 U | 3/1990 |
| JP | 2257960 A | 10/1990 |
| JP | H4-003375 U1 | 1/1992 |
| JP | 0749211 A | 2/1995 |
| JP | 7050569 A | 2/1995 |
| JP | H7-115212 A | 5/1995 |
| JP | 9061363 A | 3/1997 |
| JP | 10201827 A | 8/1998 |
| JP | 2002507279 A | 3/2002 |
| JP | 2002-362652 A | 12/2002 |
| JP | 2007093586 A | 4/2007 |
| JP | 2012119448 A | 6/2012 |
| JP | 2014038055 A | 2/2014 |
| JP | 2015-062438 A | 4/2015 |
| WO | 2008/004212 A2 | 1/2008 |
| WO | 2010023430 A1 | 3/2010 |

OTHER PUBLICATIONS

The Decision of Refusal dated Feb. 19, 2019 of Japanese Patent Application No. 2017-081177.
The Decision of Rejection of Amendment(1)(2) dated Feb. 19, 2019 of Japanese Patent Application No. 2017-081177.
Office Action dated Mar. 19, 2020 in Chinese Patent Application No. 201780023413, with English translation.

* cited by examiner

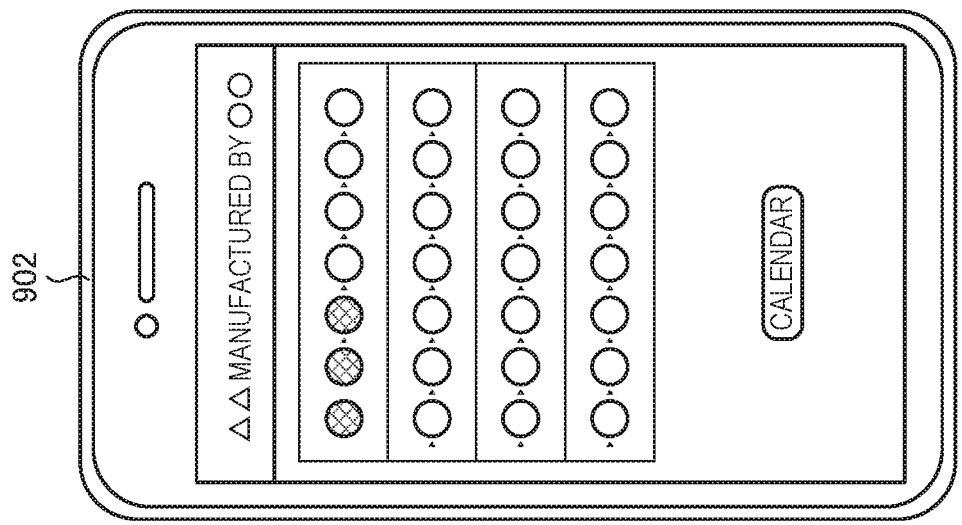
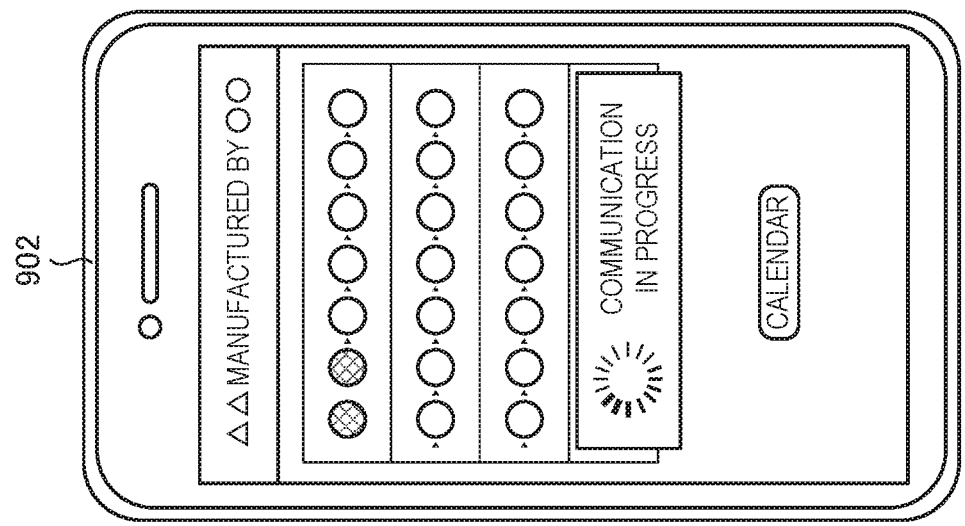
FIG. 17

DETECTION APPARATUS FOR DETECTING TAKING-OUT OF CONTAINED OBJECT FROM BLISTER PACK, DETECTION METHOD THEREFOR, AND MEDICATION MANAGEMENT SYSTEM

CROSS-REFERENCE TO RELATED APPLICATIONS

This application is a U.S. National Stage filing under 35 U.S.C. § 371 and 35 U.S.C. § 119 based on and claiming the benefit of PCT/JP2017/015502, filed on Apr. 17, 2017, and claiming the benefit of priority from Japanese patent application No. 2016-082135, filed on Apr. 15, 2016, and Japanese patent application No. 2017-081177, filed on Apr. 17, 2017, the disclosures of all of which are incorporated herein in their entireties by reference.

TECHNICAL FIELD

The present invention relates to a detection apparatus for detecting the taking-out of a contained object from a blister pack, a detection method therefor, and a medication management system.

BACKGROUND

In the above technical field, patent reference 1 discloses a technique of managing the taking of medicines contained in a blister pack.

Patent reference 1: Japanese Patent Laid-Open No. 2015-62438

SUMMARY OF THE INVENTION

In the technique described in reference 1, however, it is necessary to prepare a very special blister pack to manage medication. Furthermore, in general, a technique of readily detecting the taking-out of a contained object in a blister pack has been long awaited.

The present invention enables to provide a technique of solving the above-described problem.

One example aspect of the present invention provides a detection apparatus for detecting a timing at which a contained object is taken out from a blister pack including a plurality of containing portions and a plate-like portion that connects the plurality of containing portions, the apparatus comprising:

a plate on which the blister pack is arranged;

a plurality of light sources that emit light beams to the plurality of containing portions of the blister pack arranged on the plate;

a plurality of sensors that receive the light beams emitted from the light sources, and also output electrical signals corresponding to light reception intensities; and a detector that detects the presence/absence of contained objects in the respective containing portions based on the electrical signals output from the plurality of sensors.

Another example aspect of the present invention provides a detection method of detecting a timing at which a contained object is taken out from a blister pack including a plurality of containing portions and a plate-like portion that connects the plurality of containing portions, the method comprising:

detecting, using a plurality of light sources that emit light beams to the plurality of containing portions of the blister pack and a plurality of sensors that receive the light beams emitted from the light sources, and also output electrical signals corresponding to light reception intensities, the presence/absence of contained objects in the respective containing portions based on the electrical signals output from the plurality of sensors.

Still other example aspect of the present invention provides a medication management system for managing a timing at which a medicine is taken out from a blister pack including a plurality of containing portions and a plate-like portion that connects the plurality of containing portions, the system comprising:

a plate on which the blister pack is arranged;

a plurality of light sources that emit light beams to the plurality of containing portions of the blister pack arranged on the plate;

a plurality of sensors that receive the light beams emitted from the light sources, and also output electrical signals corresponding to light reception intensities;

a detector that detects the presence/absence of contained objects in the respective containing portions based on the electrical signals output from the plurality of sensors; and a display unit that displays detection results by the detector.

According to the present invention, it is possible to readily detect the taking-out of an object contained in a blister pack.

BRIEF DESCRIPTION OF DRAWINGS

FIG. 17 is a view for explaining the use method of the medication management system according to the second example embodiment of the present invention;

DESCRIPTION OF EXAMPLE EMBODIMENTS

Example embodiments of the present invention will now be described in detail with reference to the drawings. It should be noted that the relative arrangement of the components, the numerical expressions and numerical values set forth in these example embodiments do not limit the scope of the present invention unless it is specifically stated otherwise.

First Example Embodiment

Figure 1:
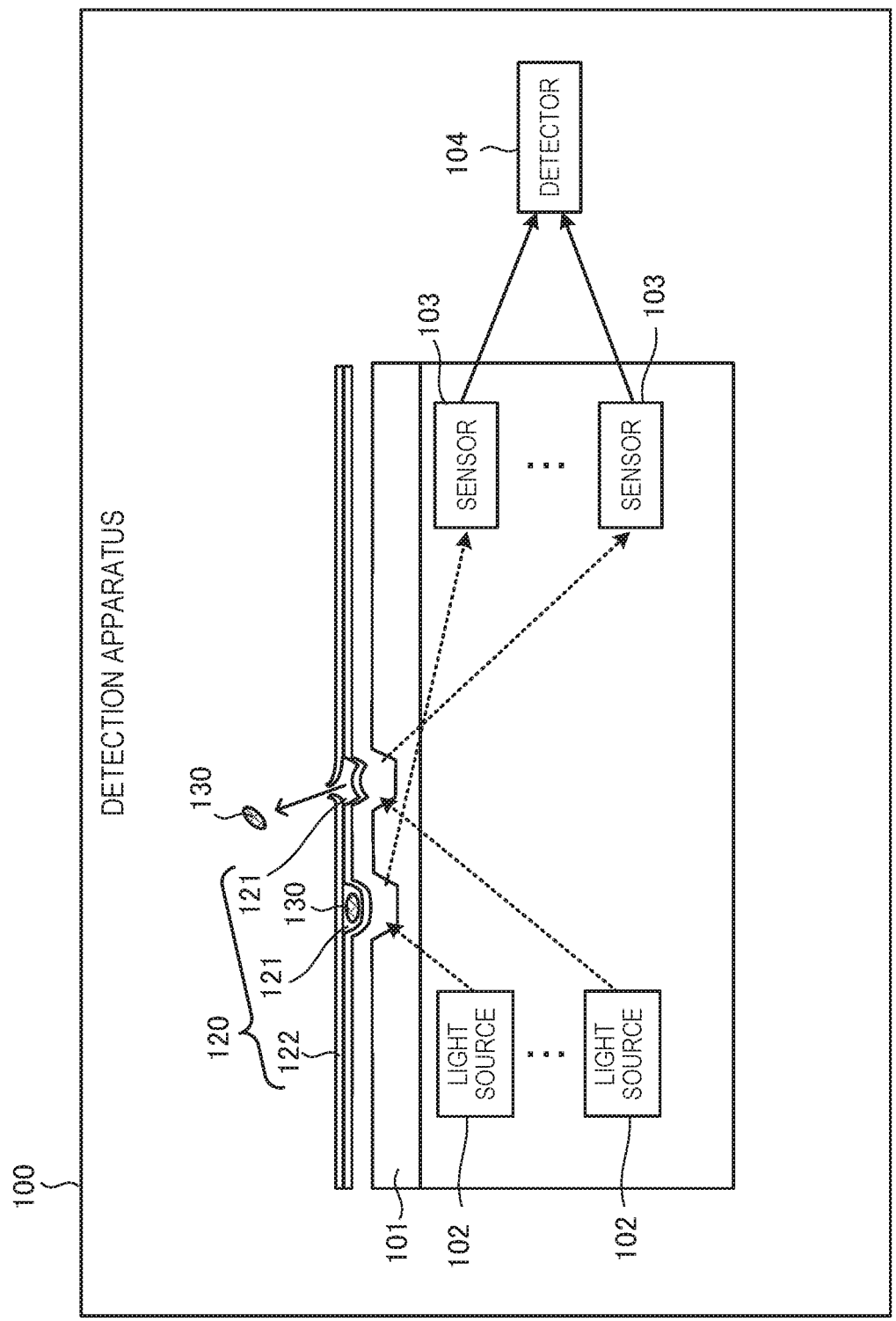
FIG. 1 is a block diagram showing the arrangement of a detection apparatus according to the first example embodiment of the present invention.

A detection apparatus 100 according to the first example embodiment of the present invention will be described with reference to FIG. 1.

The detection apparatus 100 detects the timing at which each contained object 130 is taken out from a blister pack 120 including a plurality of containing portions 121 and a plate-like portion 122 that connects the plurality of containing portions 121.

The detection apparatus 100 includes a plate 101, a plurality of light sources 102, a plurality of sensors 103, and a detector 104.

The blister pack 120 is arranged on the plate 101.

The plurality of light sources 102 emit light beams to the plurality of containing portions 121 of the blister pack 120 arranged on the plate 101, respectively.

The plurality of sensors 103 respectively receive the light beams emitted from the plurality of light sources 102, and output electrical signals corresponding to light reception intensities.

The detector 104 detects the presence/absence of the contained objects 130 in the respective containing portions 121 based on the electrical signals output from the plurality of sensors 103.

According to this example embodiment, it is possible to readily detect the timing at which each of a plurality of objects contained in a blister pack is taken out.

Second Example Embodiment

Figure 2:
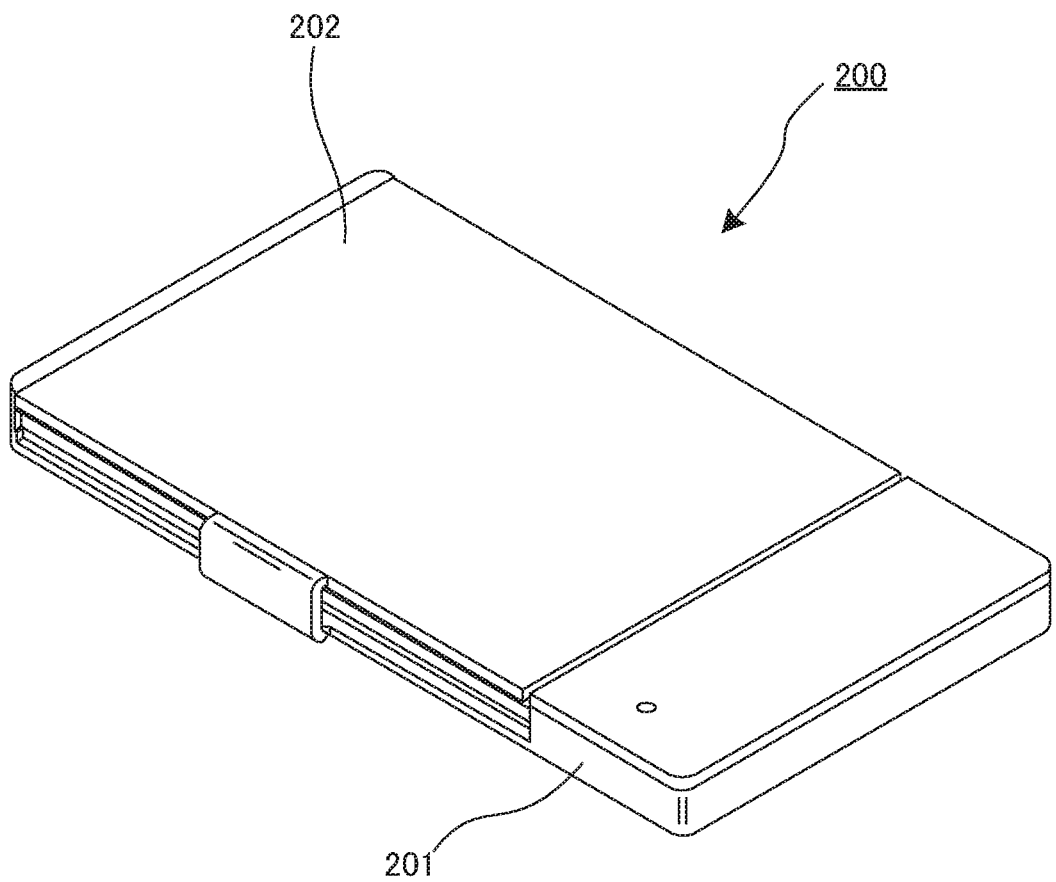
FIG. 2 is a perspective view showing a state in which the cover of a detection apparatus is closed according to the second example embodiment of the present invention.

A detection apparatus according to the second example embodiment of the present invention will be described next with reference to FIG. 2. FIG. 2 is a perspective view for explaining the outer appearance of a detection apparatus 200 according to this example embodiment. As shown in FIG. 2, the detection apparatus 200 has a thick plate shape of about A7 size corresponding to the size of a blister pack, and roughly includes a main body 201 and a cover 202 that is provided to be opened/closed by a hinge (not shown) and covers part of one surface of the main body 201.

Figure 3:
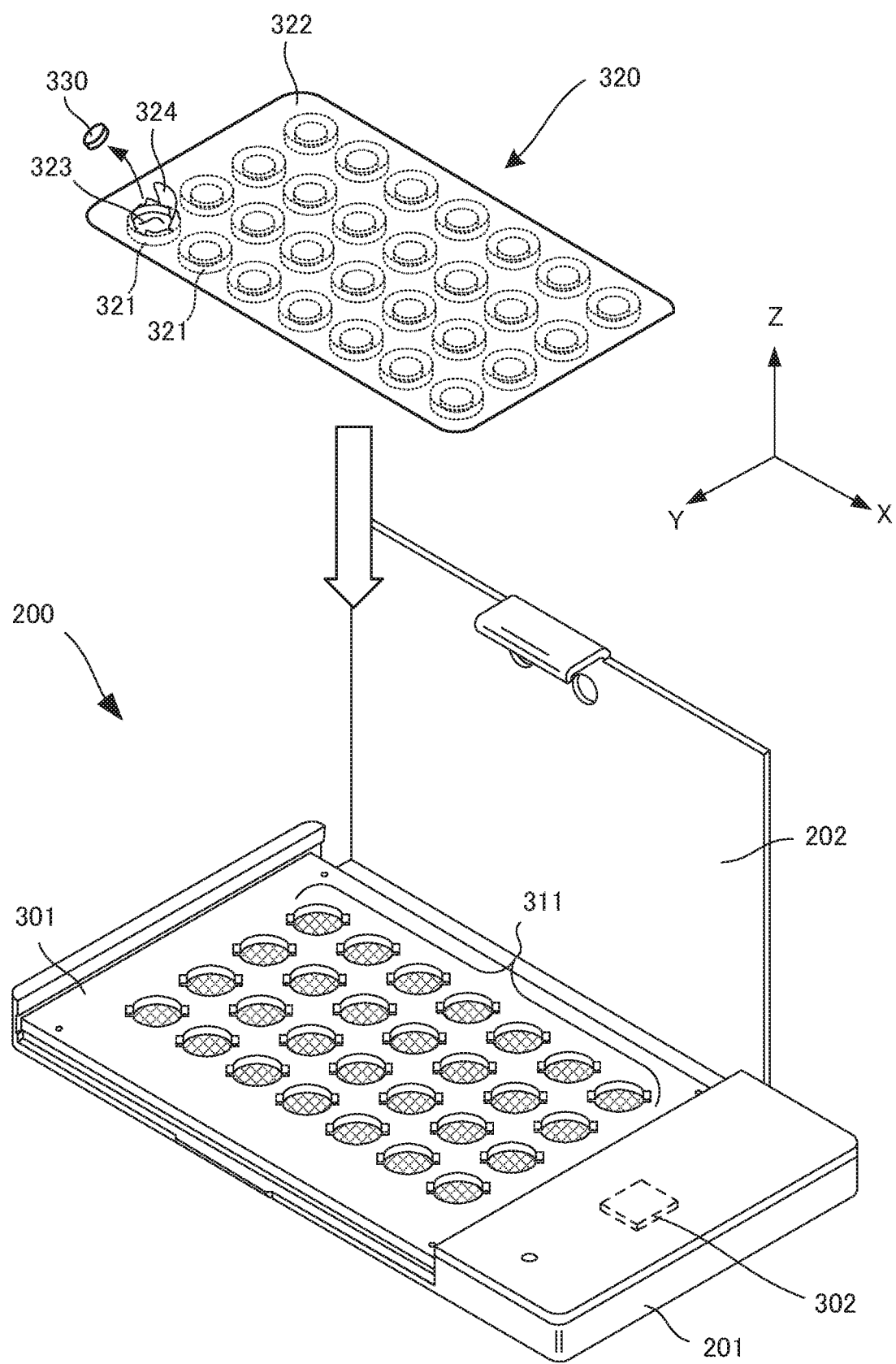
FIG. 3 is a perspective view showing a state in which the cover of the detection apparatus is open according to the second example embodiment of the present invention.

FIG. 3 is a perspective view showing a state in which the cover 202 of the detection apparatus 200 is open to arrange and attach a blister pack 320 in the detection apparatus 200.

The blister pack 320 is a so-called PTP (Press Through Pack) sheet, and includes a plurality of convex containing portions 321 and a plate-like portion 322 that connects the plurality of convex containing portions 321.

FIG. 3 shows the blister pack 320 in a state in which the plurality of convex containing portions 321 face downward, and thus the plurality of convex containing portions 321 are drawn by dotted lines. Each of the plurality of convex containing portions 321 can contain a contained object 330 (in the example of FIG. 3, a disk-like tablet).

The blister pack 320 is formed by placing the contained object 330 in each of the convex containing portions 321 formed by transparent resin moldings 323 and performing adhesion or thermocompression bonding of a sheet 324 such as aluminum foil, that is relatively easy to get ripped, to the peripheral portion of each of the convex containing portions 321.

When each transparent or translucent resin molding 323 forming each convex containing portion 321 is manually pressed upward from below in FIG. 3, the sheet 324 adhered to the upper surface of the plate-like portion 322 is ripped and the contained object 330 is taken out.

Examples of the contained object 330 of the blister pack 320 are a medicine, a quasi-drug, and a supplement, and may be a suppository other than an oral medicine. The shape may be a tablet, capsule, troche, or suppository, and the use and shape of the contained object are not limited as long as it is desirable to detect the taking-out of the contained object from a blister pack.

The main body 201 includes an arrangement unit 301 in which the blister pack 320 is to be arranged and attached. The arrangement unit 301 includes a plurality of concave portions 311, the number, positions, and sizes of which correspond to the plurality of convex containing portions 321, and has a function of positioning the blister pack 320 in the X and Y directions.

On the other hand, the cover 202 is used to press the placed blister pack 320 toward the arrangement unit 301, and has a function of positioning the blister pack 320 in the Z direction together with the arrangement unit 301. As an example, FIG. 3 shows the blister pack 320 including the 28 convex containing portions 321 in total in seven rows in the X direction and four columns in the Y direction. However, a blister pack to be detected in the present invention is not limited to this. An arrangement unit 301 that can support various types of blister packs 320 of 2 rows×5 columns and 1 row×8 columns may be adopted.

Furthermore, the main body 201 incorporates a microcontroller 302 in a side part of the arrangement unit 301, and the microcontroller 302 performs part of processing of detecting the contained objects 330 in the plurality of concave portions 311.

Figure 4:
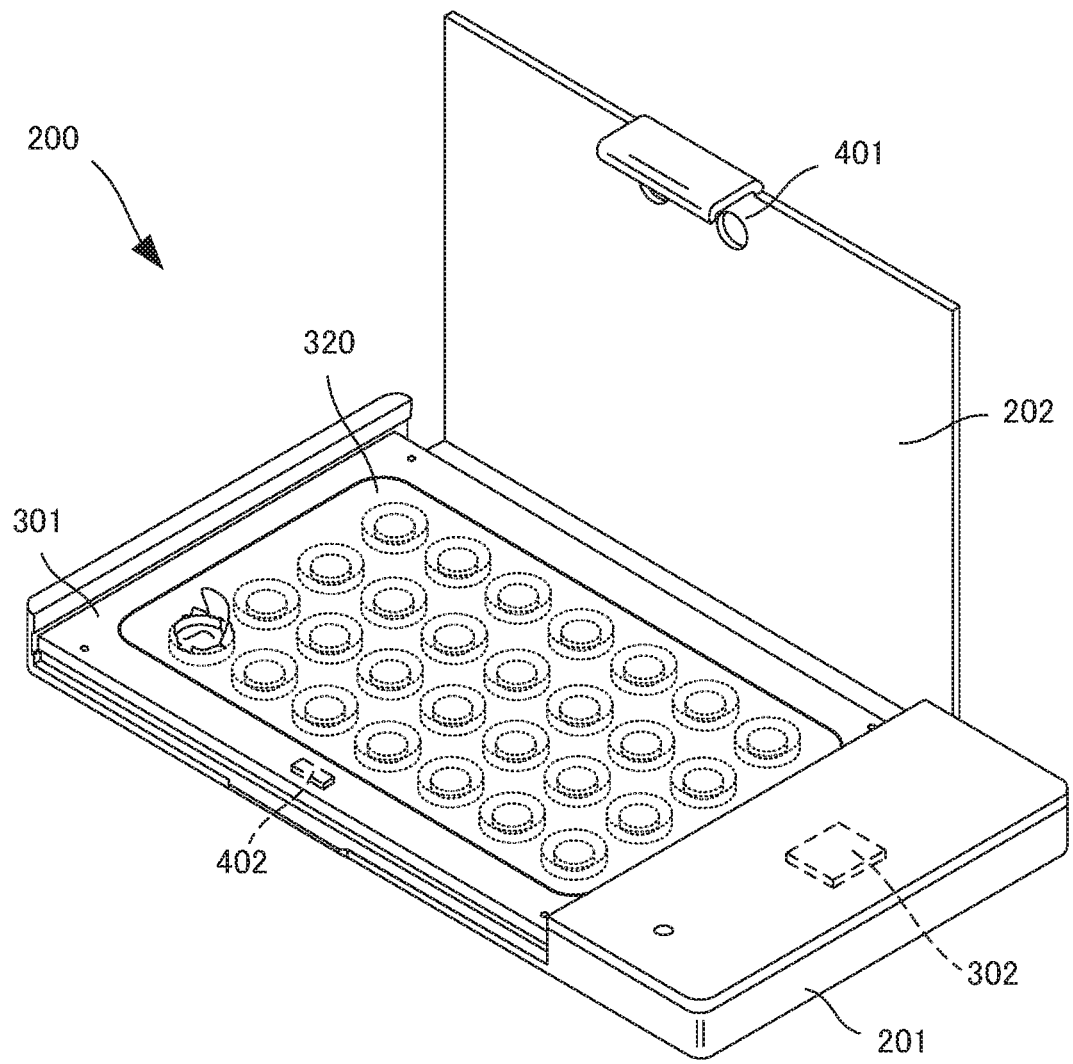
FIG. 4 is a perspective view showing a state in which a blister pack is set in the detection apparatus according to the second example embodiment of the present invention.

FIG. 4 is a perspective view showing a state in which the blister pack 320 is placed in the arrangement unit 301. The cover 202 incorporates a magnet plate 401, and a magnetic proximity sensor 402 serving as an opening/closing detector detects the opening/closing of the cover 202, and notifies the microcontroller 302 of it. The microcontroller 302 starts the processing of detecting the contained objects 330 of the blister pack 320 using, as a trigger, detection of the closing of the cover 202. Note that the combination of the magnet and the magnetic proximity sensor is used to detect the opening/closing of the cover 202. However, the present invention is not limited to this, and the opening/closing (especially, the closing) may be detected by a mechanical switch.

«Exploded View»

Figure 5:
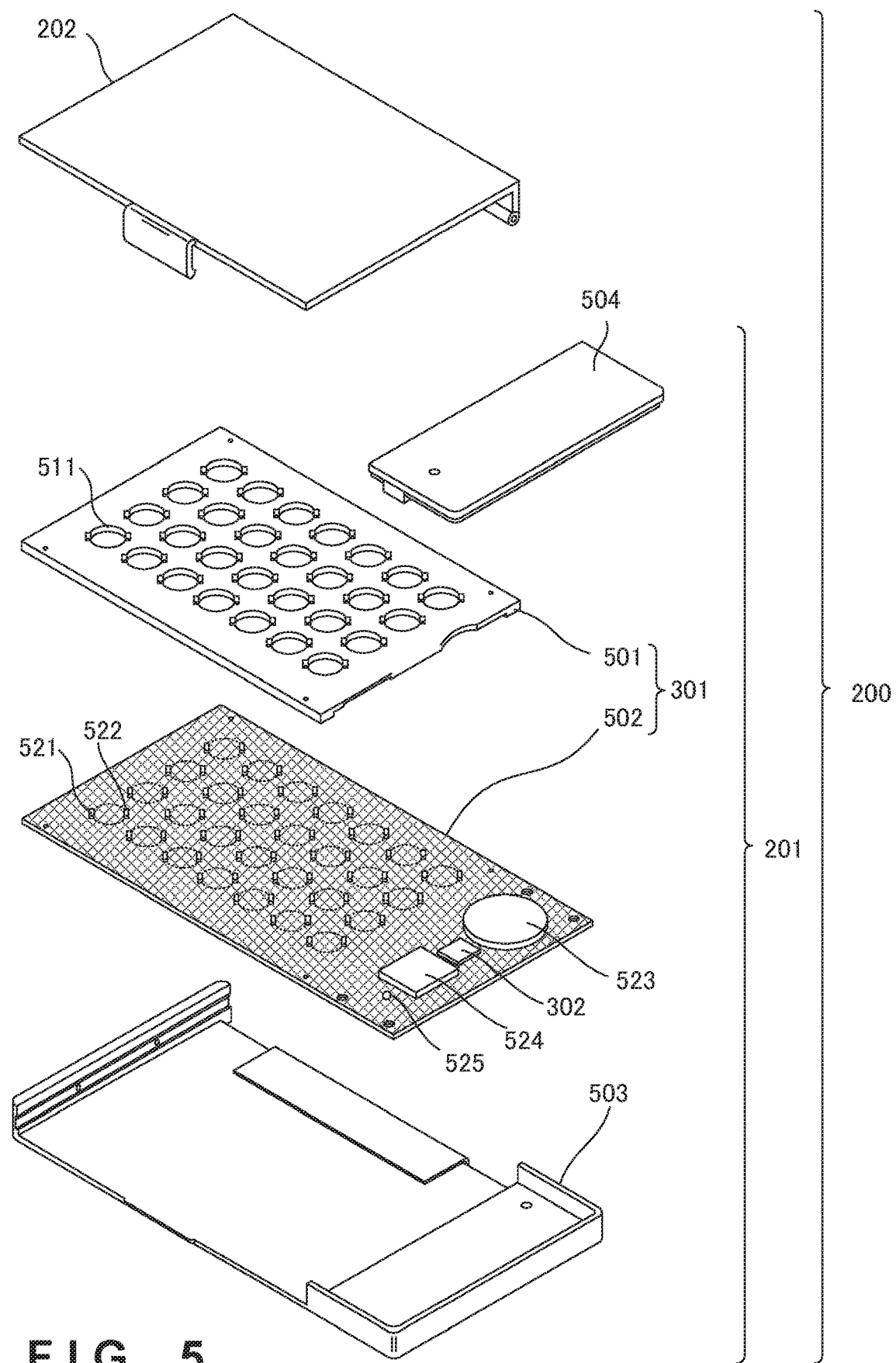
FIG. 5 is an exploded view showing the detection apparatus according to the second example embodiment of the present invention.

FIG. 5 is an exploded view showing the detection apparatus 200. The main body 201 includes a porous plate 501, a board 502, a housing 503, and a microcomputer cover 504. The porous plate 501 and the board 502 form the arrangement unit 301.

The porous plate 501 forms side wall surfaces 511 of the concave portions 311 by a plurality of through holes, and the board 502 forms the bottom surfaces of the concave portions 311.

LEDs (Light Emitting Diodes) 521 each serving as a light emitter, sensors 522, and the microcontroller 302 are provided on the board 502, and connected by an electronic circuit (lower surface). Furthermore, a button battery 523, a communication module 524 for Bluetooth® communication, and a notification LED 525 for making a notification that communication is in progress are provided on the board 502, and connected by the electronic circuit (lower surface). The microcontroller 302, the button battery 523, the communication module 524 for Bluetooth® communication, and the notification LED 525 for making a notification that communication is in progress are contained in the microcomputer cover 504 and then assembled.

When the porous plate 501 and the board 502 are assembled into a unit, all the LEDs 521 and the sensors 522 are arranged in the concave portions 311 (side wall surfaces 511). Each LED 521 emits light to each of the plurality of containing portions 321 of the blister pack 320 arranged in the arrangement unit 301.

In addition to the function of positioning the blister pack 320 in the X and Y directions, the porous plate 501 has a function of preventing the portions except for the sensors 522 from receiving the light beams emitted from the corresponding LEDs 521. That is, the porous plate 501 prevents the light beams from leaking from the concave portions 311.

That is, if the contained object 330 exists, the light emitted from each LED 521 is desirably, reliably blocked by the contained object 330 not to reach the corresponding sensor 522. For example, if the porous plate 501 has transparency, the light from the LED 521 provided in the adjacent concave portion 311 unwantedly reaches the sensor 522. Thus, the porous plate 501 is desirably made of a material with transparency as low as possible. Furthermore, each LED 521 desirably emits the light in a direction other than the direction of the corresponding sensor 522. In this example embodiment, each LED 521 emits the light upward (in the direction of the cover 202 or the sheet 324). Similarly, each sensor 522 is arranged to face in a direction in which it readily receives the light from above (from the direction of the cover 202 or the sheet 324).

To prevent the light emitted from each LED 521 from being reflected by the board 502 to reach the corresponding sensor 522, the upper surface of the board 502 desirably has a color with a low reflectance, and is black in this example embodiment.

The light emitted from each LED 521 may be linear light, and need not be diffused in the concave portion 311. Therefore, the side wall surfaces 511 may be black.

Each sensor 522 receives the light emitted from the corresponding LED 521, and outputs an electrical signal corresponding to the light reception intensity.

The microcontroller 302 time-divisionally drives the plurality of LEDs 521, and cause them to emit light beams at different timings. On the other hand, the microcontroller 302 detects the presence/absence of the contained object 330 in each of the containing portions 321 of the blister pack 320 in accordance with whether the strength of the electrical signal received from a corresponding one of the plurality of sensors 522 exceeds a predetermined threshold.

The communication module 524 outputs detection results to an external apparatus such as a smartphone using a radio wave. By installing predetermined medication management software in the smartphone or the like, the smartphone that has received the detection results can perform medication management. That is, it is possible to detect a specific timing at which the contained object 330 is taken out from a specific containing portion 321 of the blister pack 320, and can perform medication management of, for example, whether the user takes a predetermined number of tablets at decided time every day or whether the user takes a tablet for every predetermined time.

The housing 503 is formed to have a size and shape so as to contain the porous plate 501 and the board 502, and attached with the microcomputer cover 504 from above.

Figure 6:
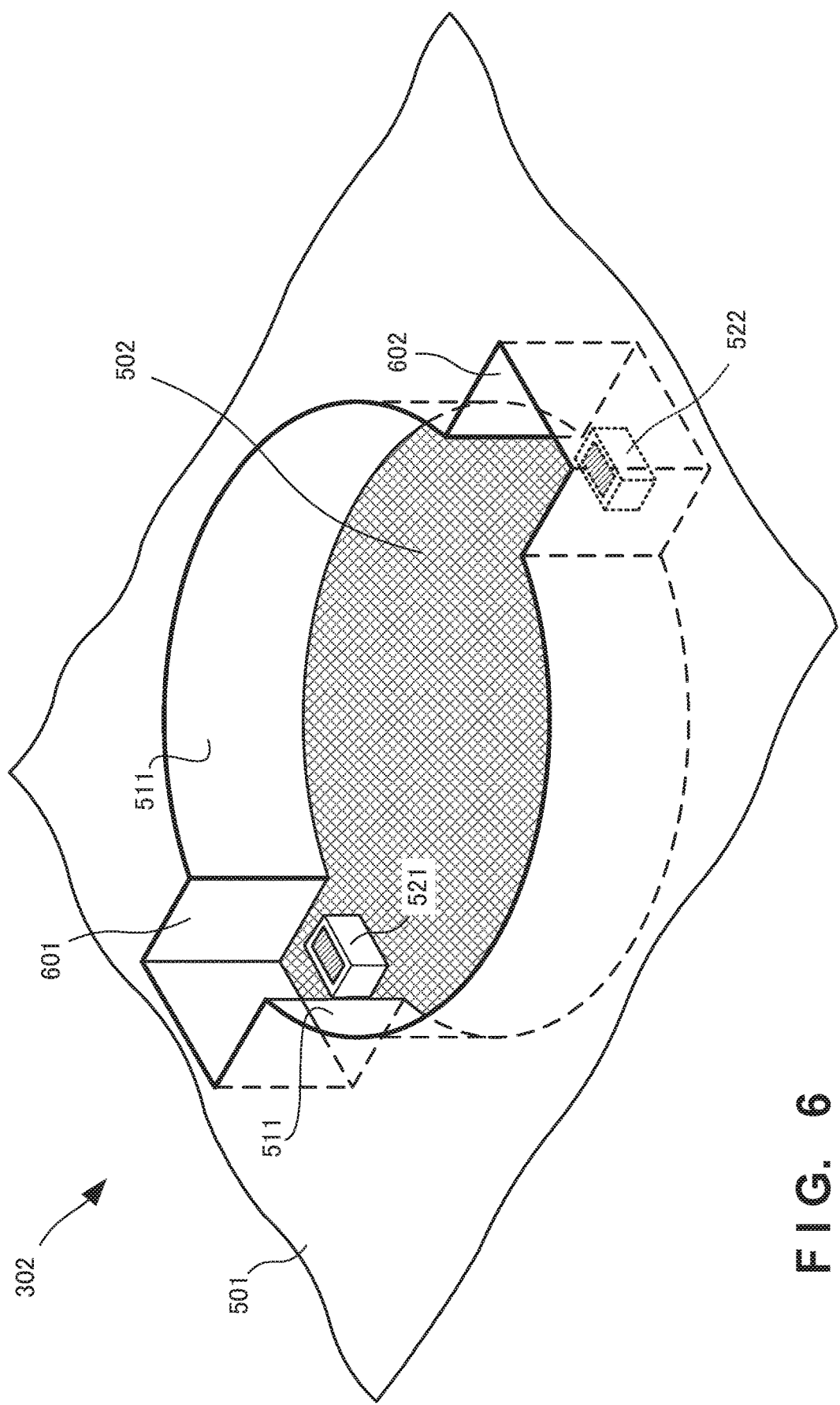
FIG. 6 is an enlarged view showing a concave portion of the detection apparatus according to the second example embodiment of the present invention.

FIG. 6 is an enlarged view showing the concave portion 311. In addition to the side wall surfaces 511, the concave portion 311 includes two notched portions 601 and 602 in which the LED 521 and the sensor 522 are arranged, respectively. The LED 521 and the sensor 522 are attached to face upward (the inner surface of the cover 202 in the closed state), and arranged so that the LED 521 emits the light toward the blister pack 320 while preventing the light emitted from the LED 521 from entering the sensor 522 directly.

«Optical Path»

Figure 7:
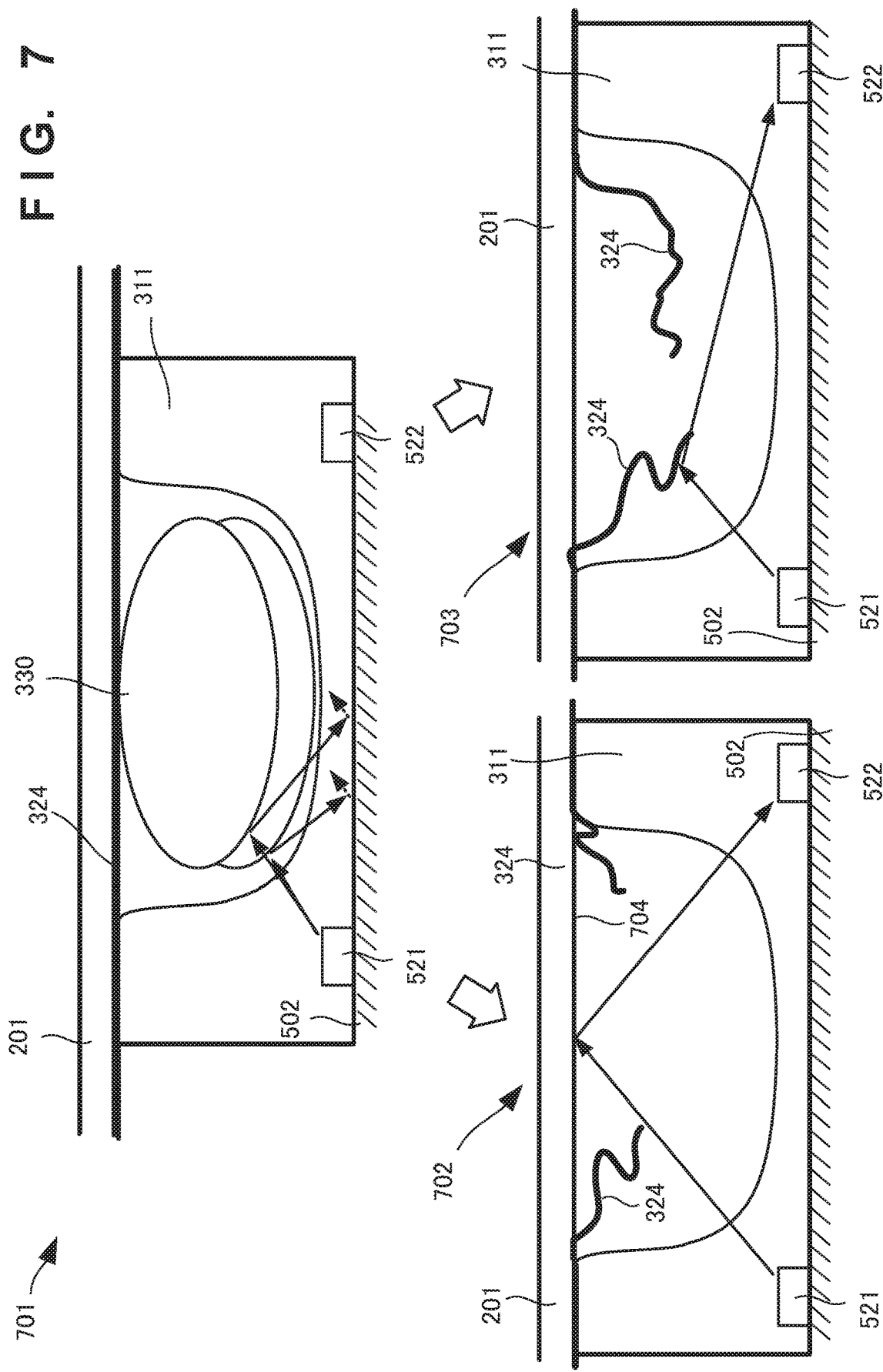
FIG. 7 is a view for explaining the contained object detection principle of the detection apparatus according to the second example embodiment of the present invention.

FIG. 7 is a sectional view of the concave portion 311 for explaining an optical path from the LED 521 to the sensor 522. In a state 701 in which the contained object 330 is in the concave portion, as shown in the upper portion, the light emitted from the LED 521 is blocked by the contained object 330, and prevented from entering the sensor 522. The light reflected by the surface of the contained object 330 or the resin molding 323 is absorbed by the black surface of the board 502 not to reach the sensor 522.

On the other hand, in a state 702 or 703 in which no contained object 330 is in the concave portion, as shown in the lower portion, the light emitted from the LED 521 is reflected by an inner surface 704 of the cover 202, the sheet 324 hanging down inside, or the like to enter the sensor 522. The inner surface 704 of the cover 202 desirably has a color (white or metallic color) with a high reflectance so that the light is reflected reliably toward the sensor 522 in the state 702 or 703 in which no contained object 330 is contained.

«Circuit»

Figure 8:
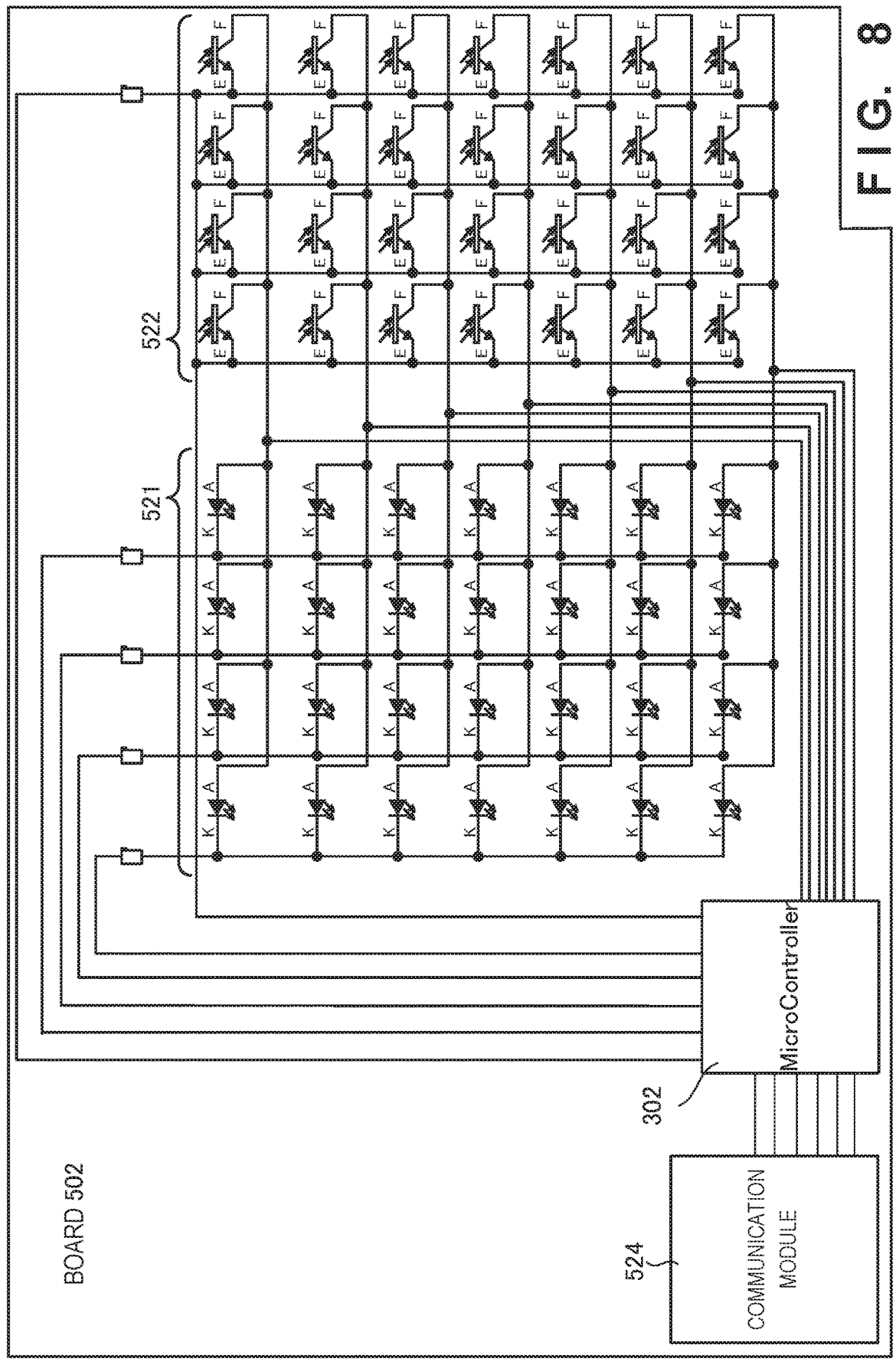
FIG. 8 is a circuit diagram showing the detection apparatus according to the second example embodiment of the present invention.

FIG. 8 is a circuit diagram showing the schematic arrangement of a circuit provided in the board 502. As shown in FIG. 8, all the LEDs 521 are connected to the microcontroller 302 individually, and controlled separately. On the other hand, as for the sensors 522, the four sensors 522 included in one row are activated simultaneously, and it is possible to detect entering of the light in one of the four sensors 522. By adopting such arrangement in which the four sensors 522 are collectively controlled, it is possible to decrease the number of terminals of the microcontroller 302, thereby using the smaller microcontroller 302. On the other hand, as long as there are no restrictions on the size and cost of the apparatus, all the sensors 522 may be controlled separately. In this case, the LED 521 and sensor 522 of each of the 28 pairs are controlled at the same timing.

In the microcontroller 302, 28-bit data as detection result information of each of the 28 sensors 522 is combined with data (32-bit time stamp) indicating relative time, thereby obtaining one piece of detection result information. Then, a predetermined number (for example, 20) of pieces of detection result information are stored in the microcontroller 302. With this processing, even if communication with an external apparatus fails, pieces of information each indicating the presence/absence of the contained object 330 in each of the convex containing portions 321 of the blister pack 320 are temporarily stored in the microcontroller 302, and are collectively sent when communication with the external apparatus succeeds next time. For example, the external apparatus sequentially receives the pieces of detection information from the latest one, and compares it with the time stamp of storage information stored in the external apparatus, thereby receiving the past taking-out history of the contained objects 330 completely. Note that the time stamp of the microcontroller 302 is overwritten with the time of the external apparatus every time communication with the external apparatus is performed.

«Use Method»

A use method of the detection apparatus 200 will be described in detail with reference to FIGS. 9 to 17.

Figure 9:
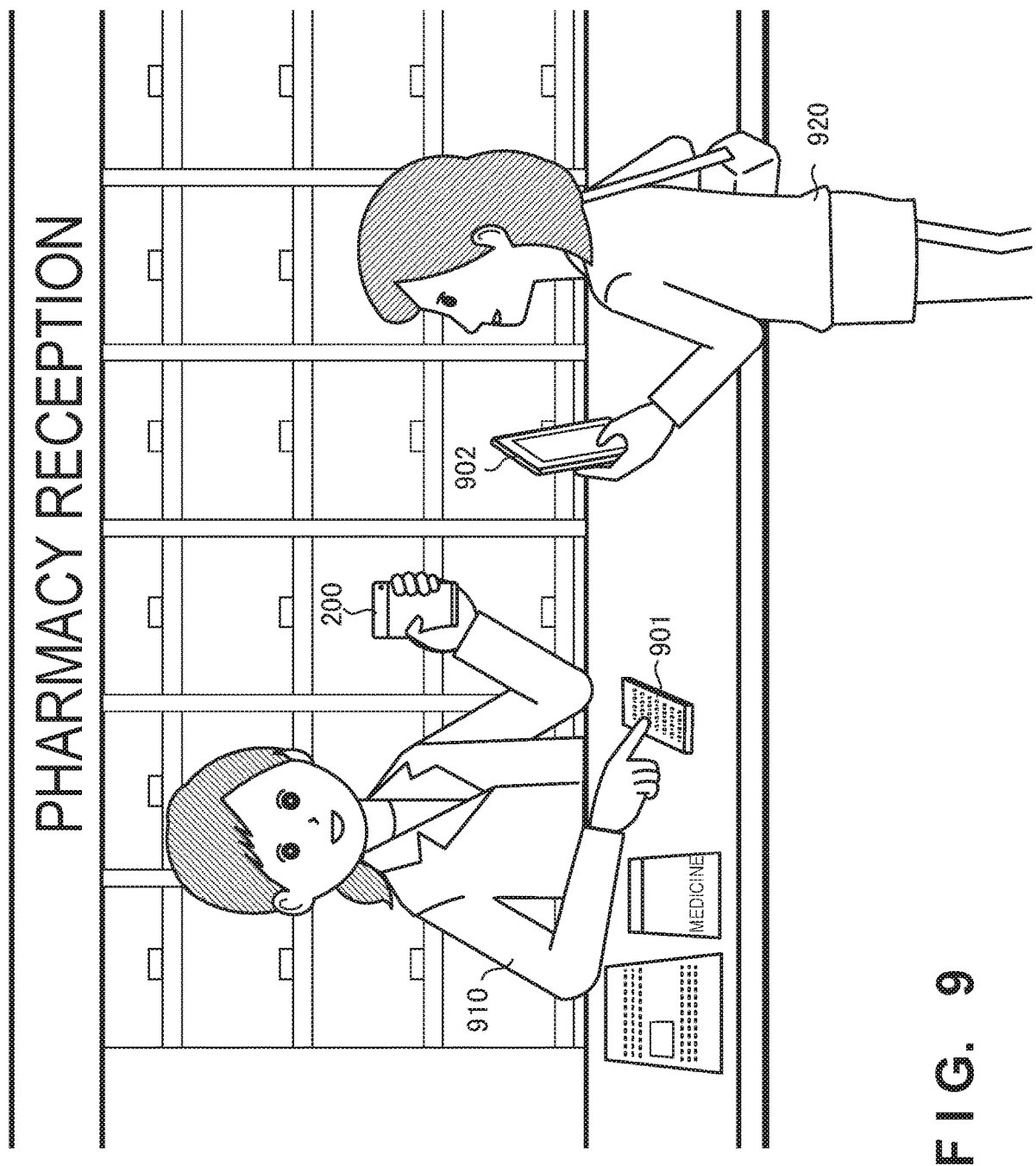
FIG. 9 is a view for explaining a use method of the detection apparatus according to the second example embodiment of the present invention.

As shown in FIG. 9, in a pharmacy, a patient 920 receives medicines together with the detection apparatus 200 from a pharmacist 910, and receives an explanation of a use method. In addition, a predetermined application program is downloaded to a user terminal 902 such as a smartphone held by the patient 920.

As an example, a case in which the patient receives a three-fold sheet incorporating the blister pack 320, which is called a wallet package 901, and takes a tablet regularly will be described. The inner and outer surfaces of the wallet package 901 can be used as additional printing surfaces for displaying information, and the wallet package 901 has a function capable of preventing a child or old person from erroneously taking a medicine.

Figure 10:
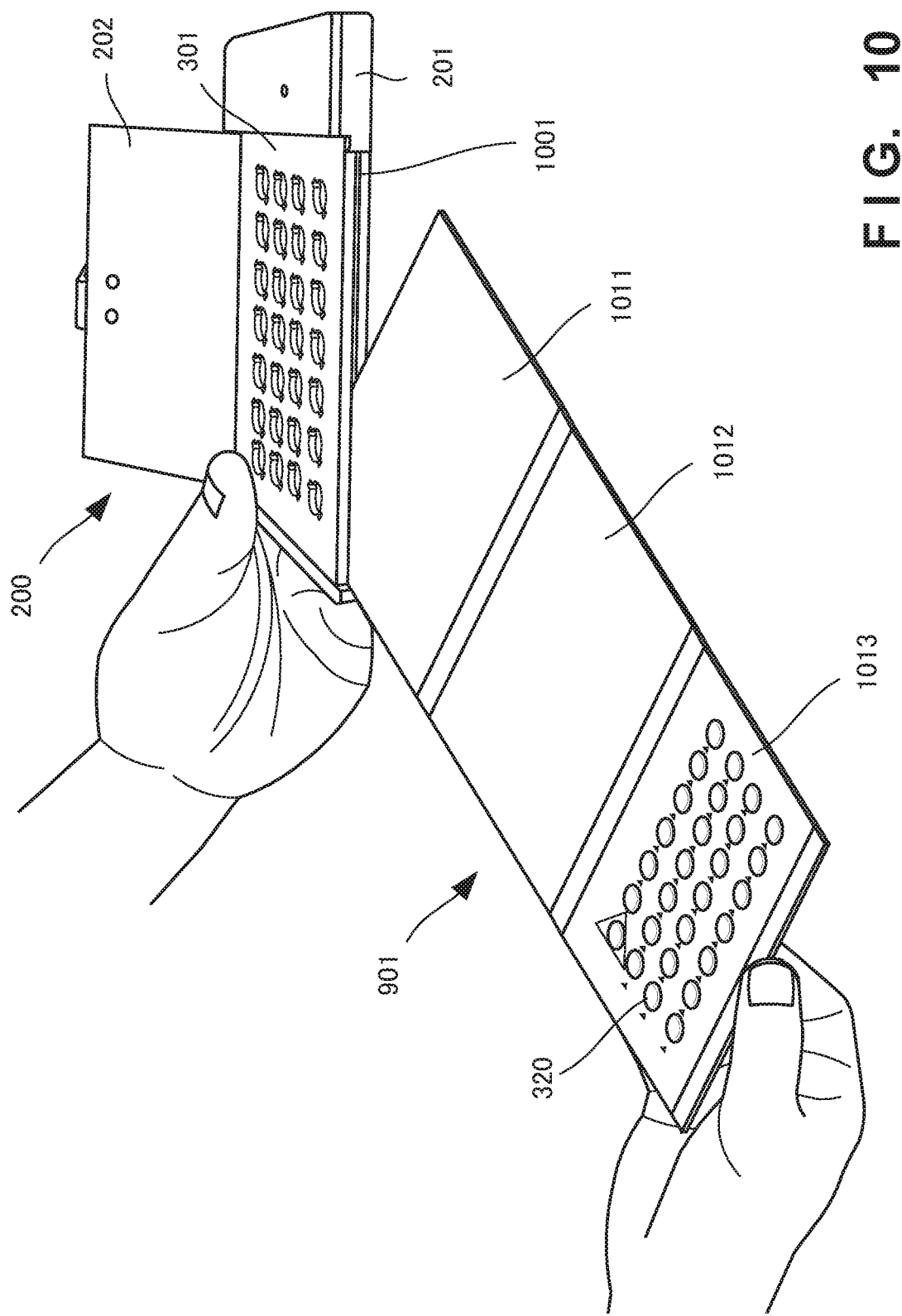
FIG. 10 is a view for explaining the use method of the detection apparatus according to the second example embodiment of the present invention.
Figure 11:
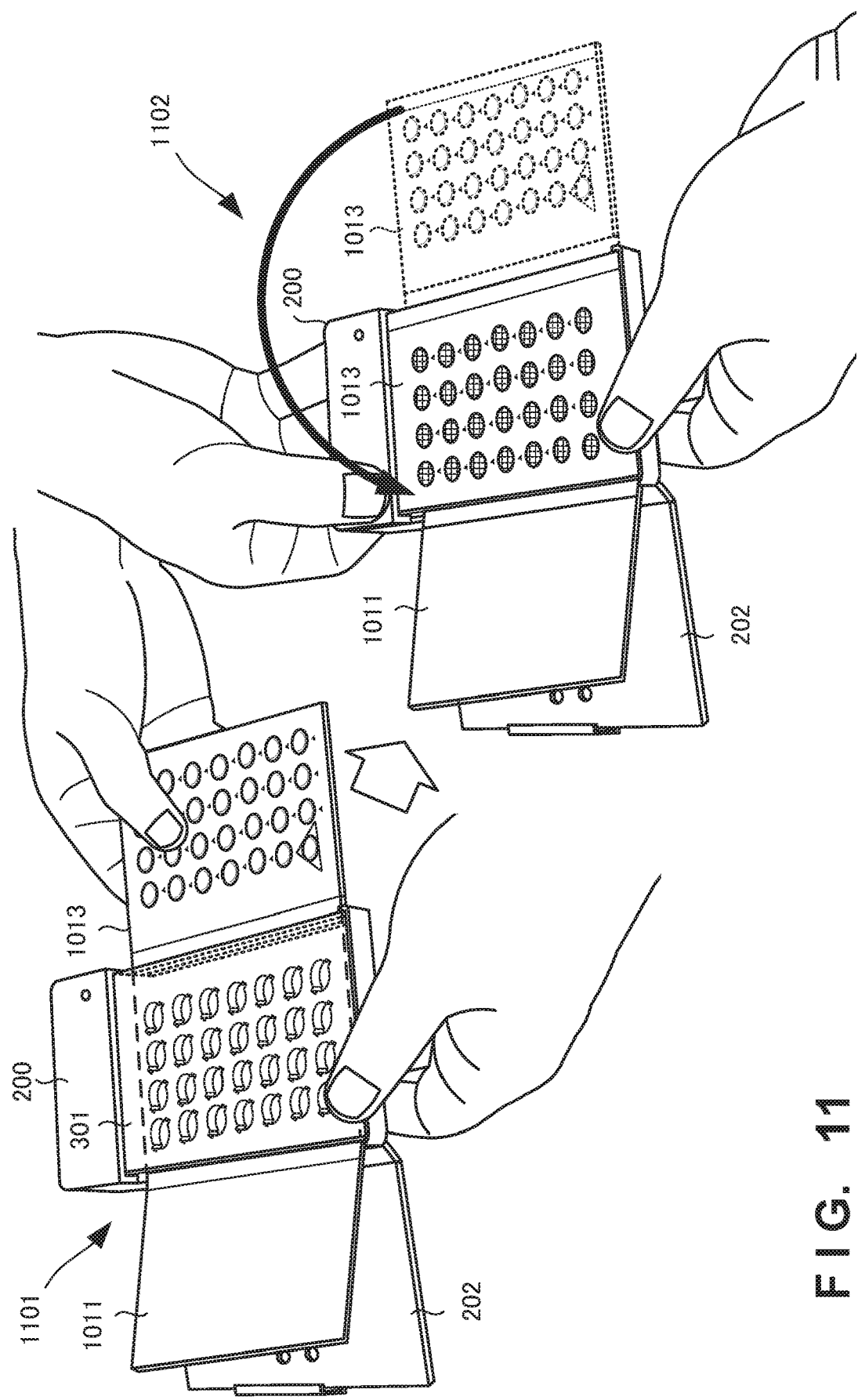
FIG. 11 is a view for explaining the use method of the detection apparatus according to the second example embodiment of the present invention.

As shown in FIG. 10, if the wallet package 901 incorporating the blister pack 320 is opened, three continuous sheets 1011 to 1013 are obtained. The patient who has received the wallet package 901 inserts, among the three sheets 1011 to 1013, the sheets 1011 and 1012 which incorporate no blister pack 320 into a slit 1001 provided on the lower side of the arrangement unit 301 of the main body 201 in the state in which the cover 202 is open.

The slit 1001 extends to the side of the cover 202. Thus, if the wallet package 901 is pressed, the sheet 1011 appears in front of the cover 202, as shown in a state 1101 of FIG. 11.

Next, as shown in a state 1102, the sheet 1013 incorporating the blister pack 320 is folded to arrange the blister pack 320 at a predetermined position on the arrangement unit 301.

Figure 12:
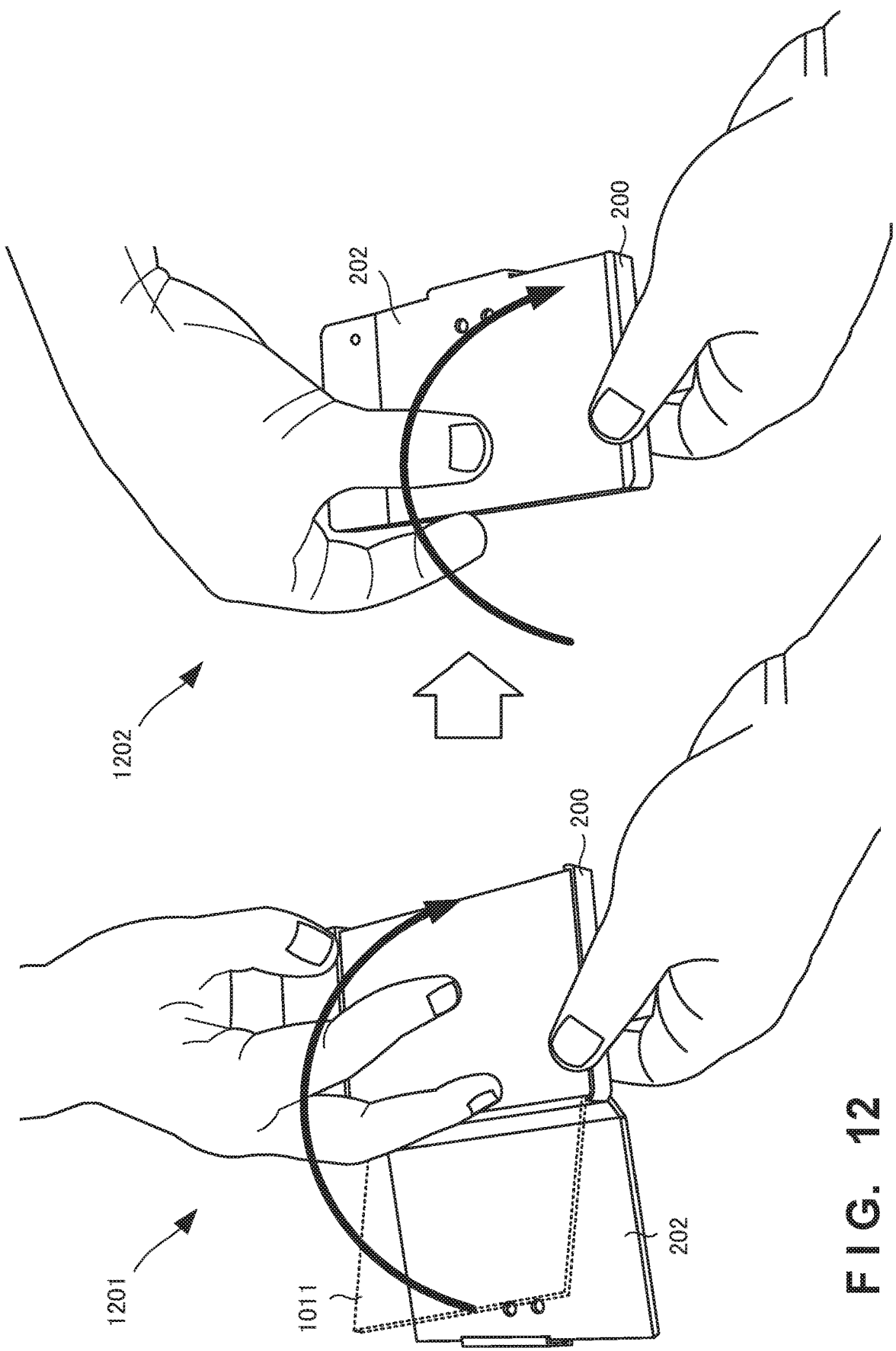
FIG. 12 is a view for explaining the use method of the detection apparatus according to the second example embodiment of the present invention.

Furthermore, as shown in a state 1201 of FIG. 12, the sheet 1011 is folded and superimposed on the sheet 1011. After that, as shown in a state 1202, the cover 202 is closed and pressed from above by a finger, thereby positioning the blister pack 320 in the Z direction.

Figure 13:
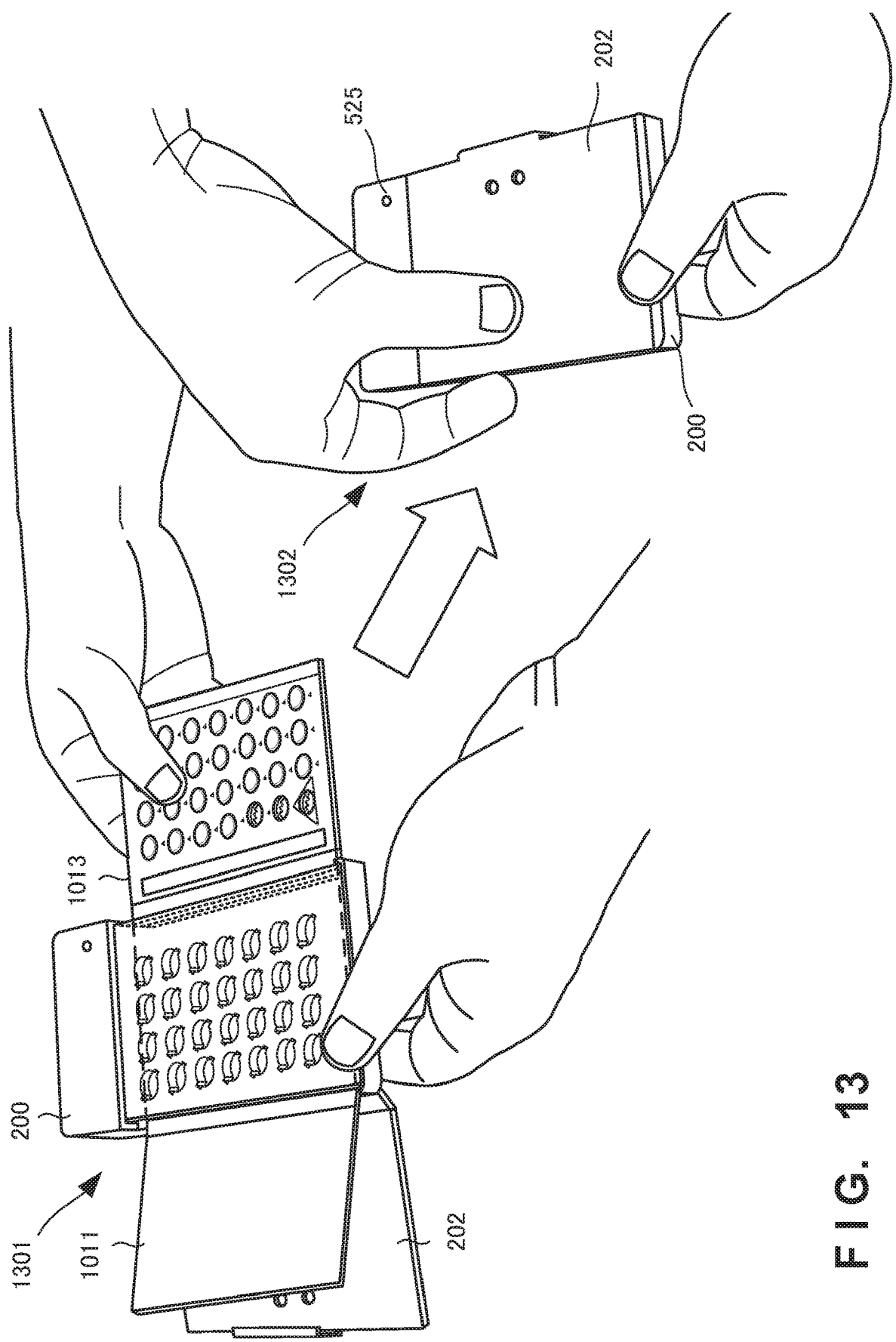
FIG. 13 is a view for explaining the use method of the detection apparatus according to the second example embodiment of the present invention.

When taking a tablet, as shown in a state 1301 of FIG. 13, the sheets 1011 and 1013 are opened and the blister pack 320 is pressed, thereby taking out the tablet downward. After that, the sheets 1011 and 1013 are folded again, and the cover 202 is closed to press the blister pack 320 into the arrangement unit 301. When the closing of the cover 202 is detected, the internal devices such as the microcontroller 302, the LEDs 521, and the sensors 522 perform processing of detecting the remaining tablets, and transmit information about the positions of the remaining tablets to the external apparatus. During communication, the notification LED 525 is ON.

As described above, the slit 1001 is provided in the main body 201 and the wallet package 901 can be inserted. It is thus possible to prevent the blister pack 320 from leaving from the detection apparatus 200 when taking a medicine. Furthermore, it is possible to position the blister pack 320 accurately with respect to the arrangement unit 301, and improve the detection accuracy.

«Medication Management System»

Figure 14:
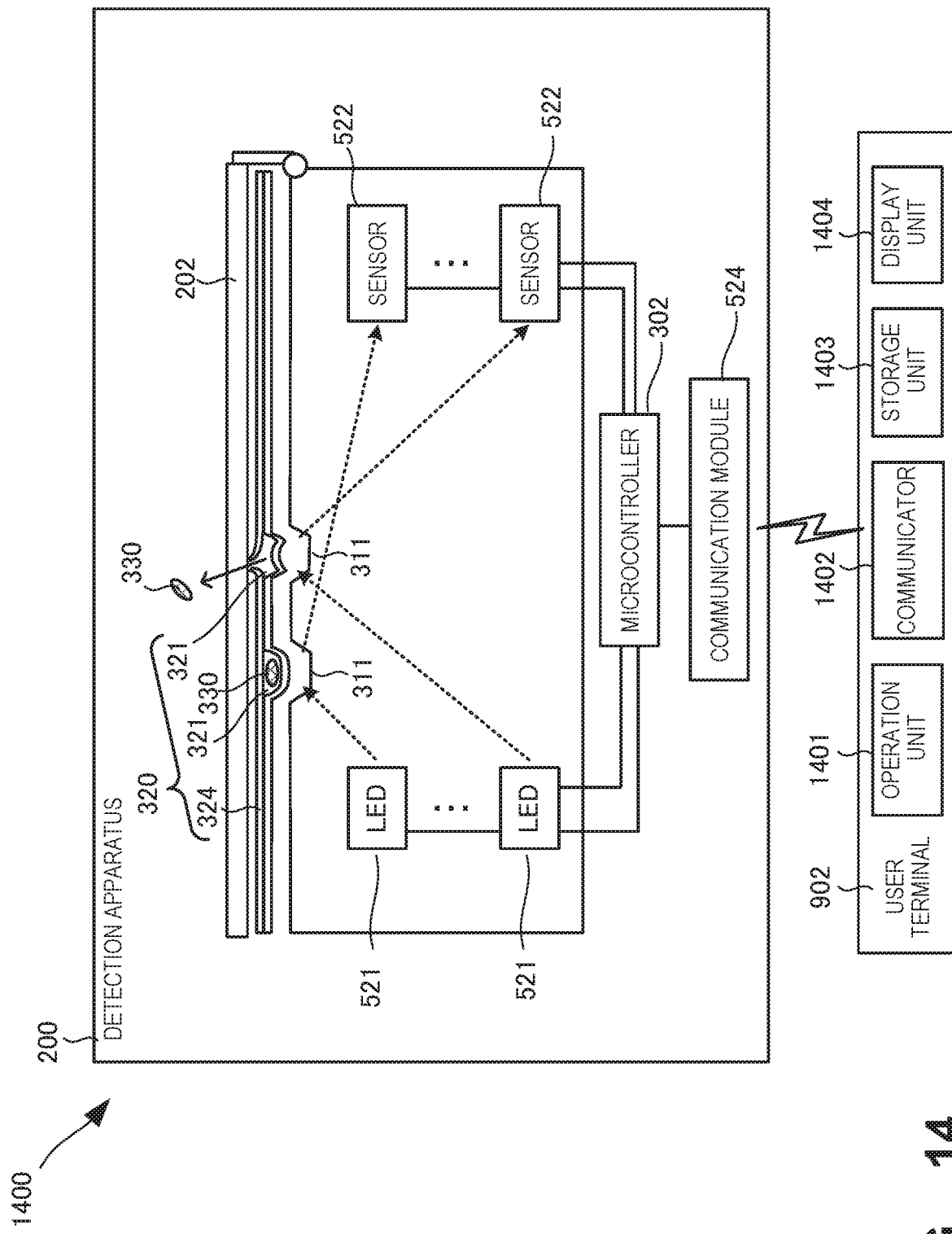
FIG. 14 is a block diagram showing the functional arrangement of a medication management system according to the second example embodiment of the present invention.

FIG. 14 is a block diagram showing the functional arrangement of a medication management system 1400 using the detection apparatus 200. Upon detecting the closing of the cover 202, the microcontroller 302 serving as a controller transmits the presence/absence of the contained objects in the blister pack 320 to a communicator 1402 of the user terminal 902 via the communication module 524 serving as a communicator. The user terminal 902 includes an operation unit 1401, a storage unit 1403, and a display unit 1404 in addition to the communicator 1402, stores detection results, and displays them in various forms in accordance with a user operation.

The user terminal 902 that receives the detection information from the detection apparatus 200 is not limited to the smartphone, and may be a mobile terminal such as a PDA, a PC, a terminal dedicated for medication management, or the like. The information may be transmitted to a server connected via a LAN, the Internet, or the like at a location away from the use place of the detection apparatus 200, instead of the user terminal 902, and the detection information may be used in a medical institution. An arrangement may be adopted, in which the detection apparatus 200 and the user terminal 902 according to this example embodiment are connected via a wire and information about the presence/absence of the contained objects such as tablets is output.

Figure 15:
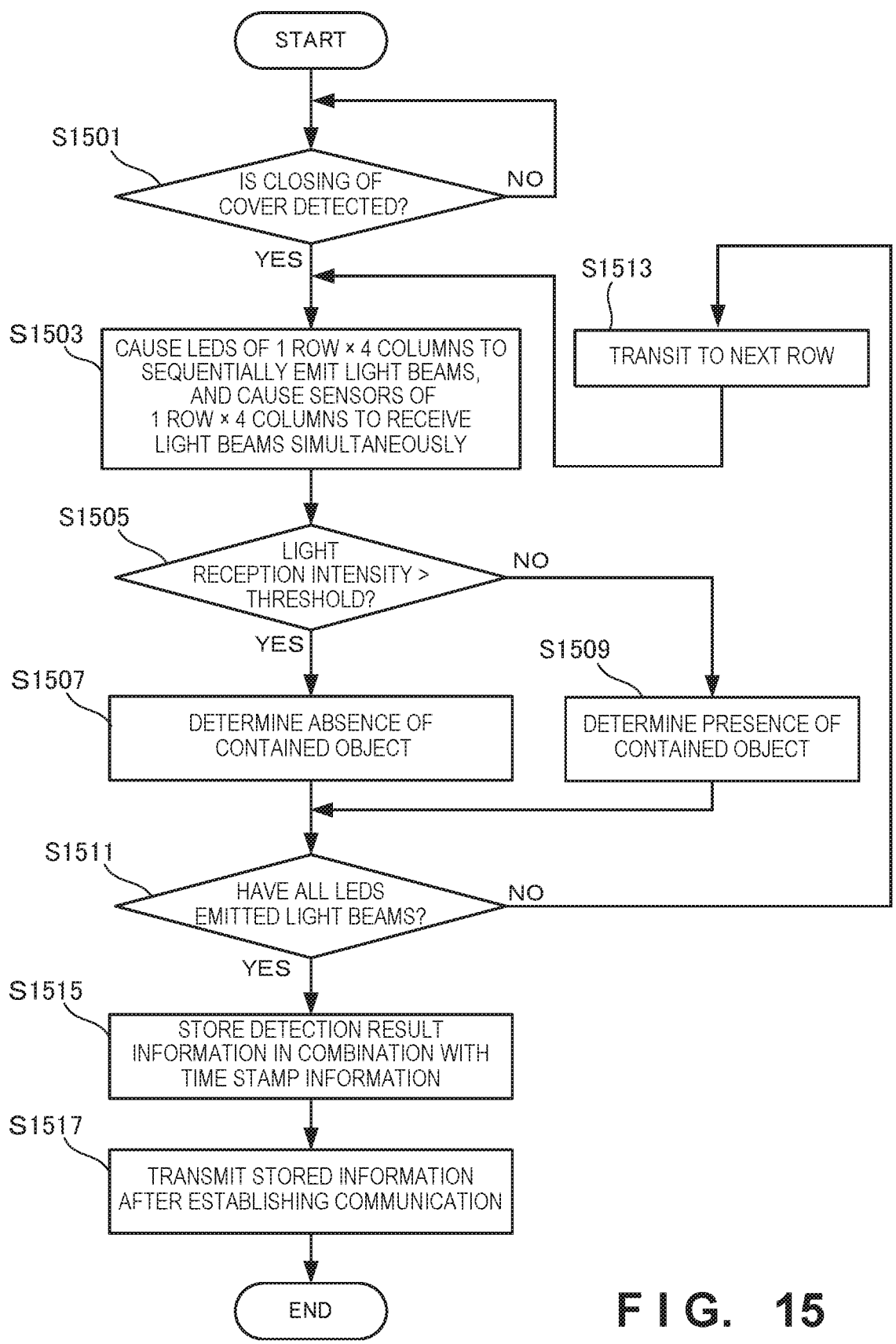
FIG. 15 is a flowchart for explaining a processing procedure of the detection apparatus according to the second example embodiment of the present invention.

FIG. 15 is a flowchart for explaining a processing procedure performed by the microcontroller 302 of the detection apparatus 200. Upon detecting the closing of the cover 202 in step S1501, in step S1503 the microcontroller 302 causes the LEDs 521 of one row (four columns in this example) to sequentially emit the light beams, and also drives the sensors 522 of the one row at the same time to measure the light reception intensities. In step S1505, each light reception intensity is compared to a threshold. If the light reception intensity is higher than the threshold, the process advances to step S1507 to determine that there is no contained object; otherwise, the process advances to step S1509 to determine that there is the contained object.

Figure 16:
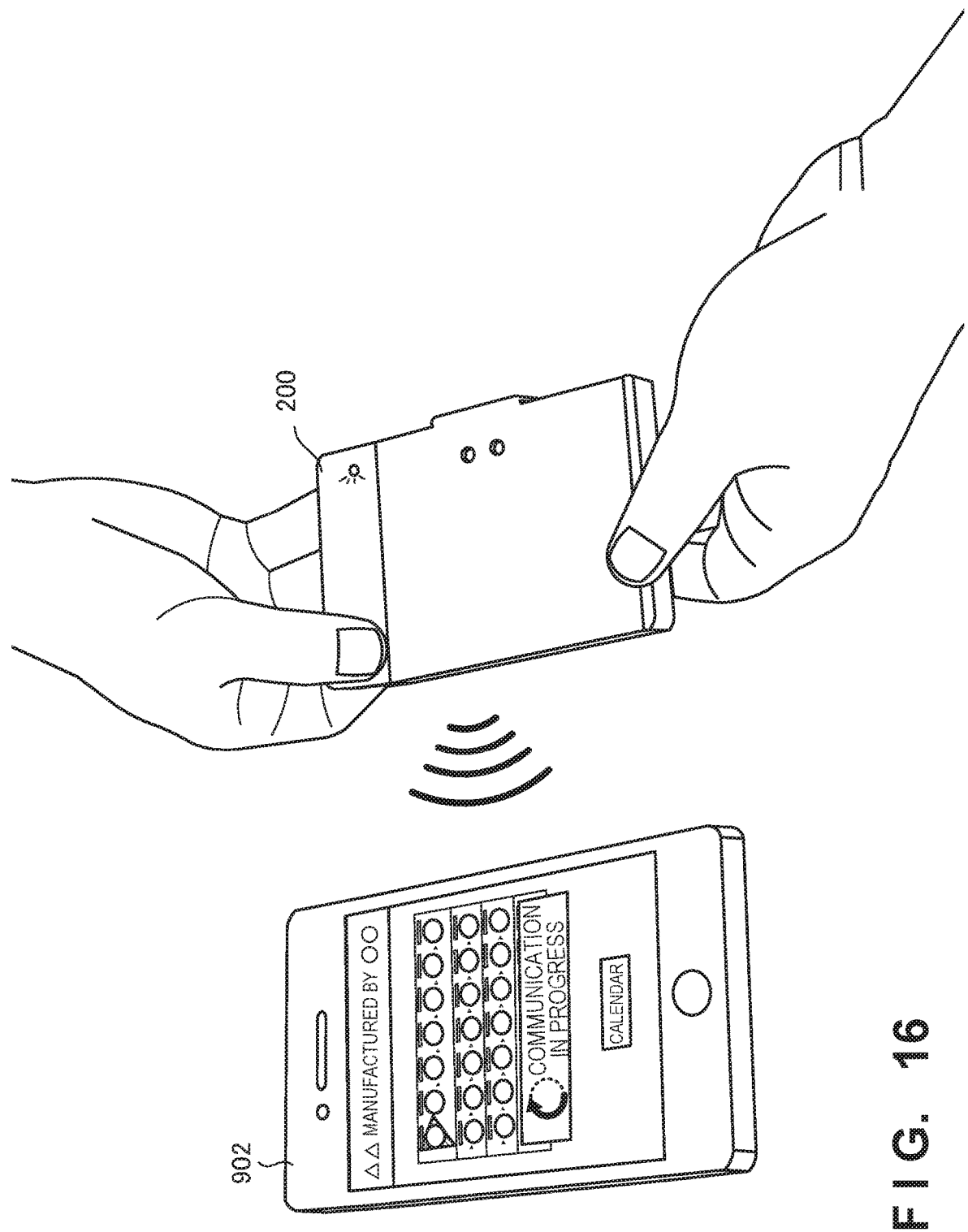
FIG. 16 is a view for explaining a use method of the medication management system according to the second example embodiment of the present invention.

If it is determined in step S1511 that not all the LEDs 521 have emitted the light beams, the process advances to the next row in step S1513, thereby driving the LEDs 521 and the sensors 522. If all the LEDs 521 have emitted the light beams, the process advances to step S1515 to store, in combination with time stamps, detection result information obtained by arraying determination results each of which represents the presence/absence of the contained object and the number of which is equal to that of LEDs 521 (that is, the containing portions). Finally, the process advances to step S1517. If the communication module 524 is driven to establish communication with a paired external apparatus, the storage information in the microcontroller 302 is transmitted in response to a request from the external apparatus. At this time, as shown in FIG. 16, the notification LED 525 is turned on simultaneously.

Display is performed on the user terminal 902 as an external apparatus, as shown in FIG. 17, thereby displaying a position on the blister pack 320 at which the contained object (tablet) has been taken out. If calendar display is selected, the screen transits to a screen shown in FIG. 18 to display the number of contained objects (tablets) which have been taken out on a specific day.

According to this example embodiment, it is possible to readily detect a specific timing at which a specific object contained in the blister pack is taken out.

Third Example Embodiment

Figure 19:
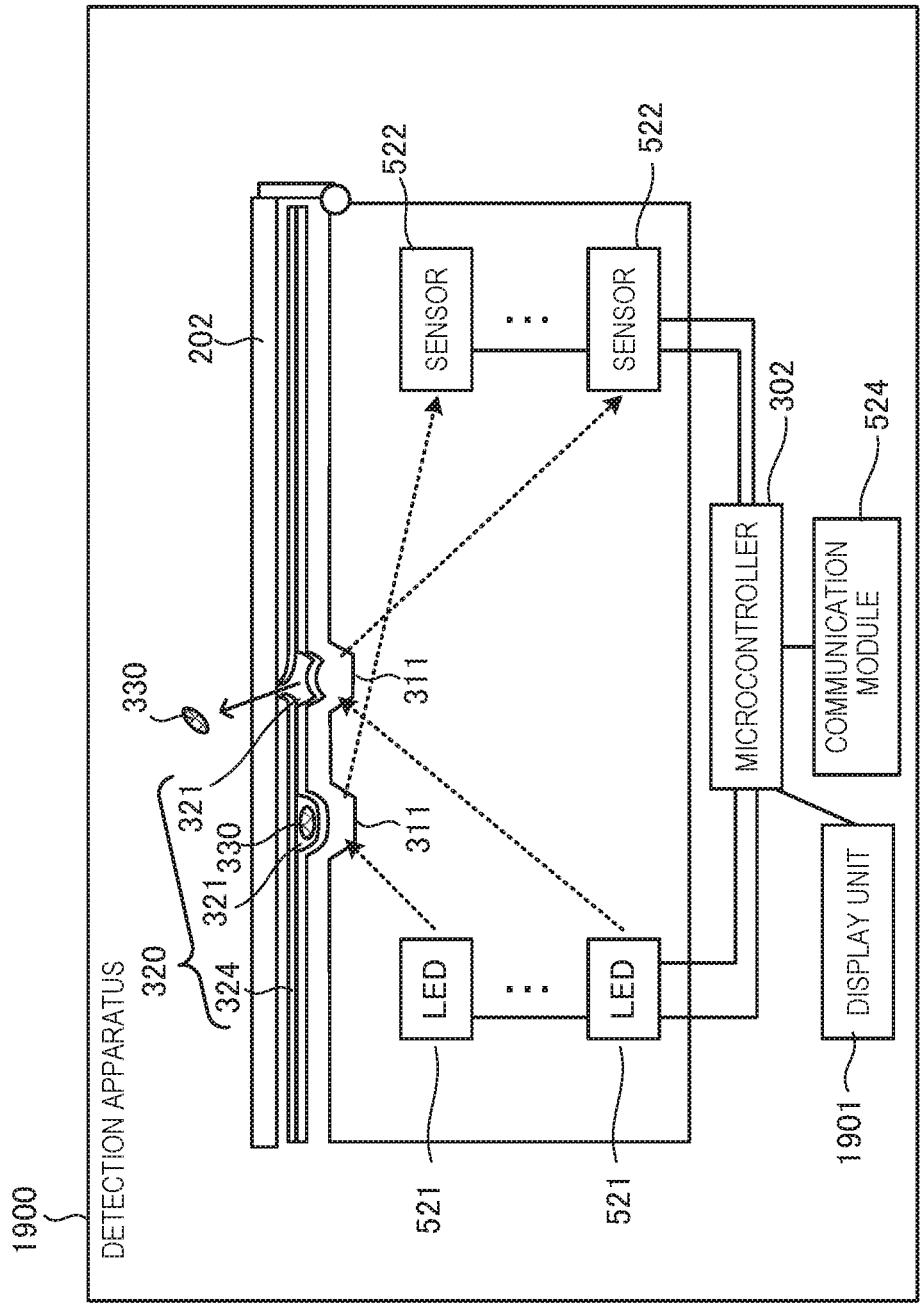
FIG. 19 is a block diagram showing the arrangement of a detection apparatus according to the third example embodiment of the present invention.

A detection apparatus according to the third example embodiment of the present invention will be described with reference to FIG. 19. FIG. 19 is a block diagram for explaining the functional arrangement of the detection apparatus according to this example embodiment. The detection apparatus according to this example embodiment is different from the above-described second example embodiment in that a display unit 1901 is included. The remaining components and operations are the same as those in the second example embodiment. Hence, the same reference numerals denote the same components and operations, and a detailed description thereof will be omitted.

Figure 18:
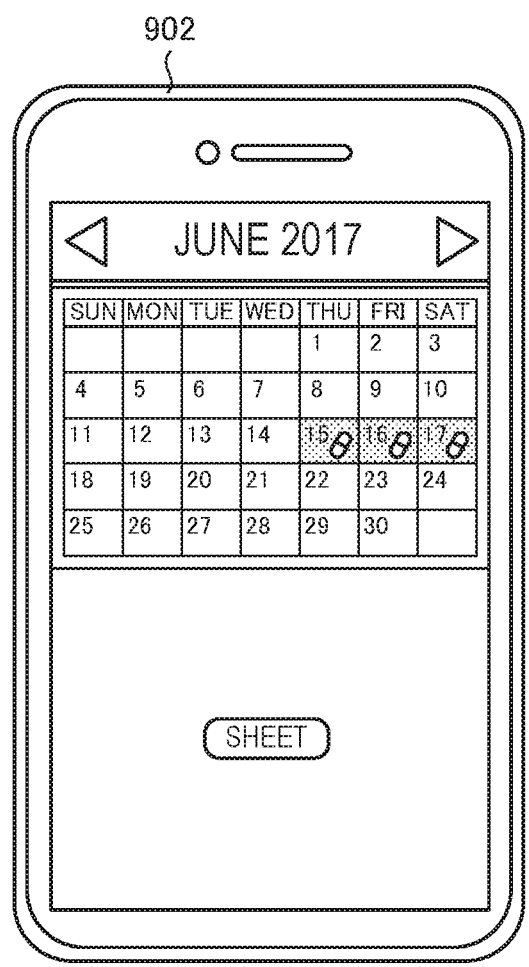
FIG. 18 is a view for explaining the use method of the medication management system according to the second example embodiment of the present invention.

Images shown in FIGS. 17 and 18 can be displayed on the display unit 1901, and it is possible to readily confirm, with a single detection apparatus 1900, a specific timing at which a specific object contained in a blister pack is taken out.

Fourth Example Embodiment

Figure 20:
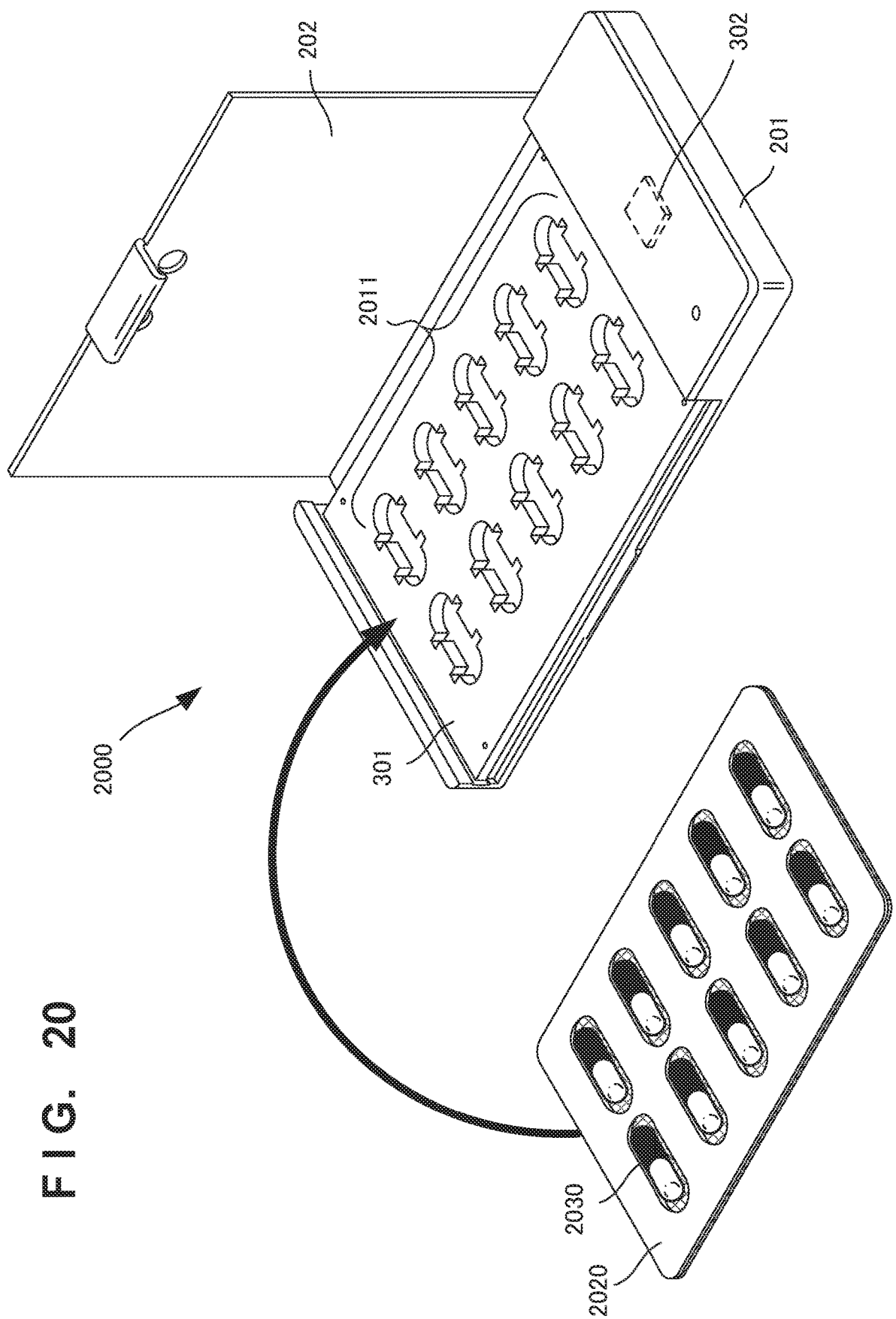
FIG. 20 is a perspective view showing a state in which the cover of a detection apparatus is open according to the fourth example embodiment of the present invention.

A detection apparatus according to the fourth example embodiment of the present invention will be described with reference to FIG. 20. FIG. 20 is an outer appearance perspective view showing a state in which a cover 202 of a detection apparatus 2000 is open according to this example embodiment. The detection apparatus 2000 according to this example embodiment is different from the above-described second example embodiment in that each concave portion 2011 formed in an arrangement unit 301 has an elliptic shape conforming to the shape of each capsule 2030, and the concave portions 2011 are arrayed in 2 rows×5 columns in accordance with the arrangement of a blister pack 2020. The remaining components and operations are the same as those in the second example embodiment. Hence, the same reference numerals denote the same components and operations, and a detailed description thereof will be omitted.

At this time, two LEDs and two sensors are arranged in each concave portion 2011 to detect the taking-out of a capsule, thereby making it possible to avoid erroneous detection.

Fifth Example Embodiment

Figure 21:
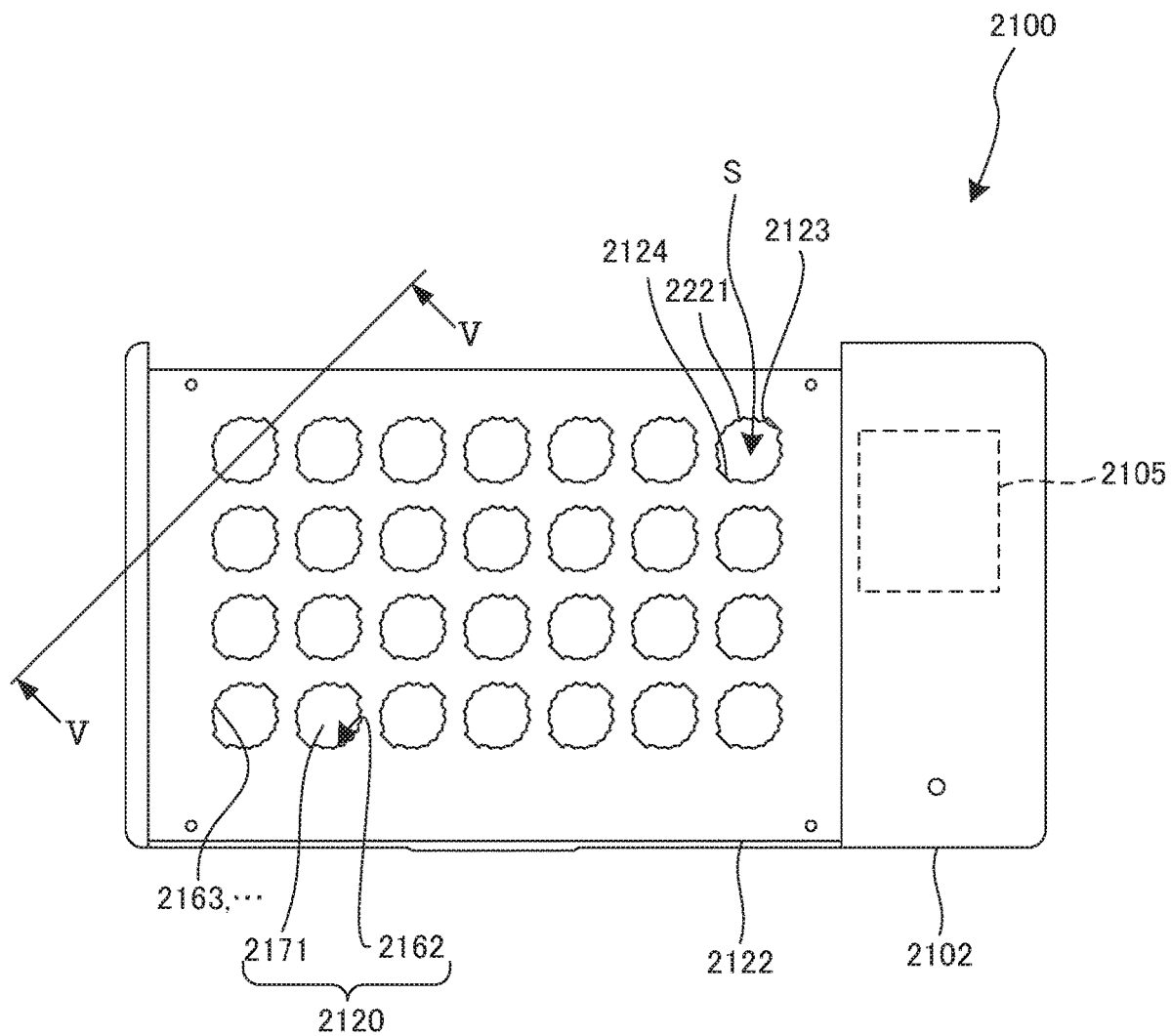
FIG. 21 is a plan view showing a state in which the cover of a detection apparatus is detached according to the fifth example embodiment of the present invention.

A detection apparatus according to the fifth example embodiment of the present invention will be described next with reference to FIGS. 21 to 26. FIG. 21 is a plan view showing a state in which the cover of a detection apparatus 2100 is detached according to this example embodiment. The detection apparatus 2100 according to this example embodiment is different from the above-described second example embodiment in that a diffuser that diffuses light emitted from a light source 2123 is included. The remaining components and operations are the same as those in the second example embodiment. Hence, the same reference numerals denote the same components and operations, and a detailed description thereof will be omitted.

As shown in FIGS. 21 to 26, the detection apparatus includes a capacity detector (capacity detection device) that outputs an electrical signal corresponding to the capacity (volume) of each containing portion 321 of a blister pack 320 as a detection target object, and a detector 2105 that detects the presence/absence of a contained object 330 in each containing portion 321 of the blister pack 320 by receiving the electrical signal from the capacity detector.

The capacity detector includes a containing member 2122 having inner wall surfaces 2120 each for defining a containing space S in which each containing portion 321 of the blister pack 320 is contained, the light sources 2123 that emit light beams to the containing spaces S, the diffusers that diffuse the light beams emitted from the light sources 2123, respectively, and light receivers 2124 that receive the light beams diffused in the containing spaces S and also output electrical signals of strengths corresponding to the light reception intensities. Each diffuser according to this example embodiment includes the inner wall surface 2120.

A main body 2102 includes a housing 2221, the containing member 2122 including the inner wall surfaces 2120, the light sources 2123, the light receivers 2124, and the detector 2105. In the main body 2102 according to this example embodiment, the plurality of containing spaces S (the number of which corresponds to that of containing portions 321 of the blister pack 320) are formed. That is, the containing member 2122 includes the plurality of inner wall surfaces 2120. The plurality of inner wall surfaces 2120 are arranged at positions corresponding to the plurality of containing portions 321 of the blister pack 320, respectively.

The containing member 2122 is a rectangular plate-like member, and includes a defining member main body 2226 having a plurality of through holes (the number of which corresponds to that of containing portions 321 of the blister pack 320) that extend through in the thickness direction, and a board 2227 that closes one opening of each through hole. In the containing member 2122 according to this example embodiment, each inner wall surface 2120 is formed by a cylindrical circumferential surface portion 2162 for defining the through hole, and a portion (closing portion) 2171 for closing one opening of the through hole on the board 2227. That is, each of the plurality of inner wall surface 2120 includes the circumferential surface portion 2162 and the closing portion 2171. Each inner wall surface 2120 according to this example embodiment has an opening, and also has a shape such that the containing space S becomes a closed space when an opening peripheral portion 2223 of the inner wall surface 2120 abuts against the periphery of the containing portion 321 of the blister pack 320 in a state in which the containing portion 321 of the blister pack 320 is inserted from the opening into the containing space S (see FIG. 24).

Figure 22:
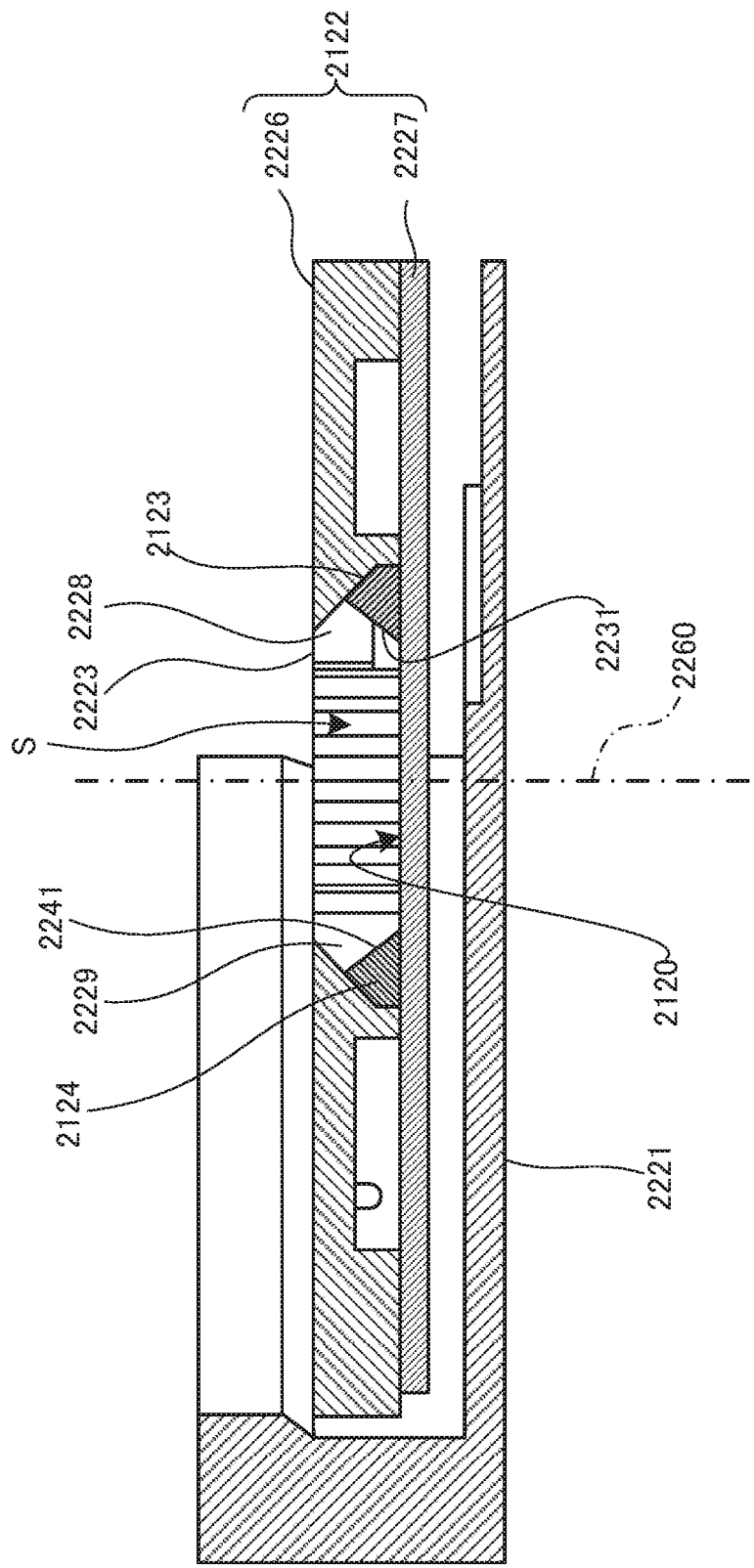
FIG. 22 is an enlarged sectional view at a V-V position in FIG. 21.
Figure 23:
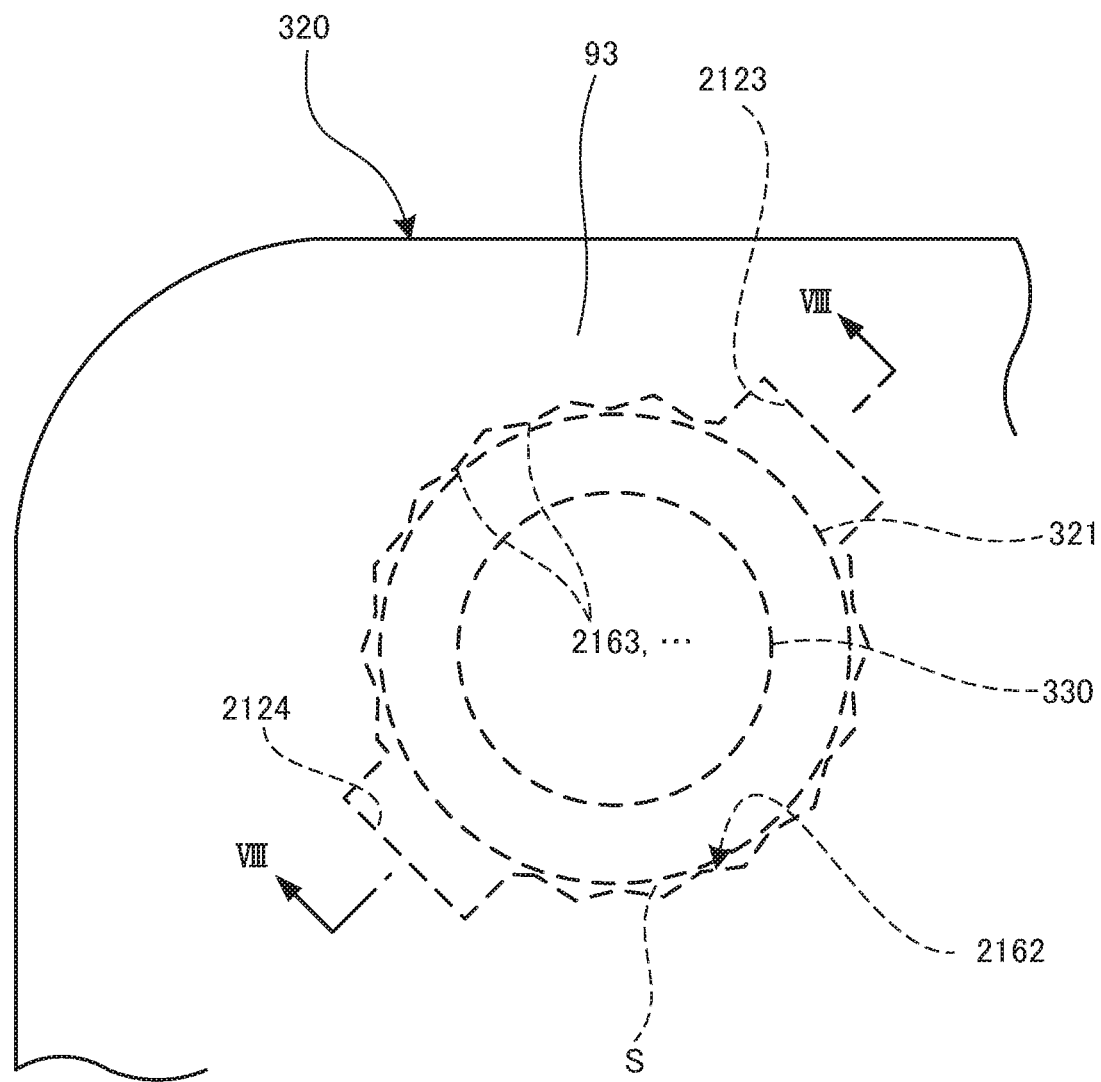
FIG. 23 is a view for explaining a state in which a containing portion of a blister pack is contained in a containing space defined by the inner wall surface of a containing member.
Figure 24:
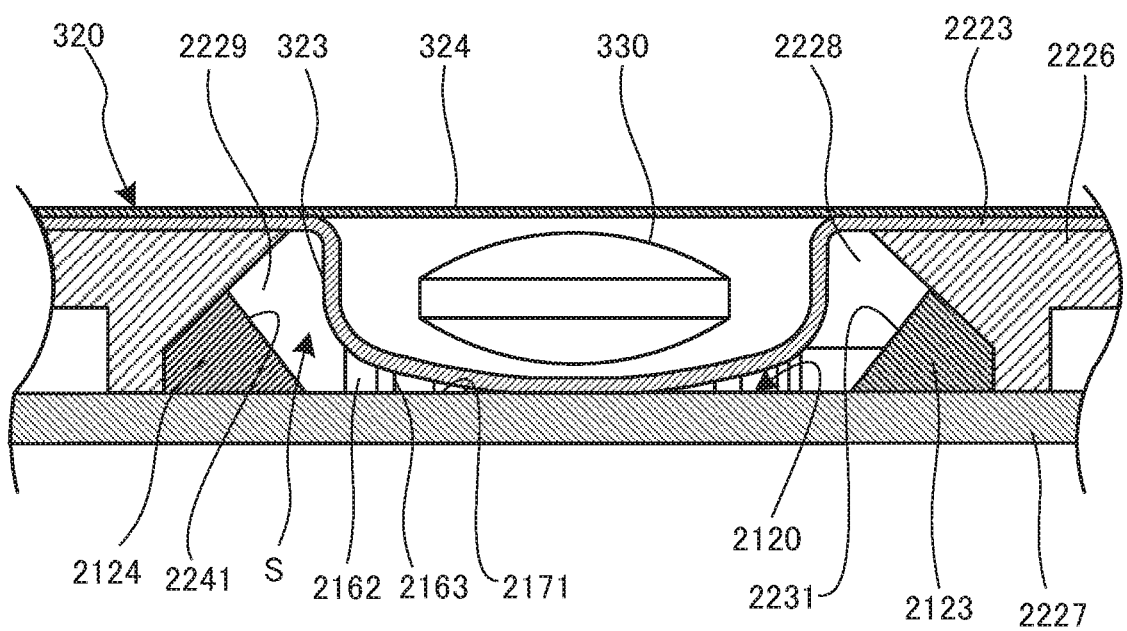
FIG. 24 is a sectional view, at a VIII-VIII position in FIG. 23, showing a state in which a contained object is contained in the containing portion.
Figure 25:
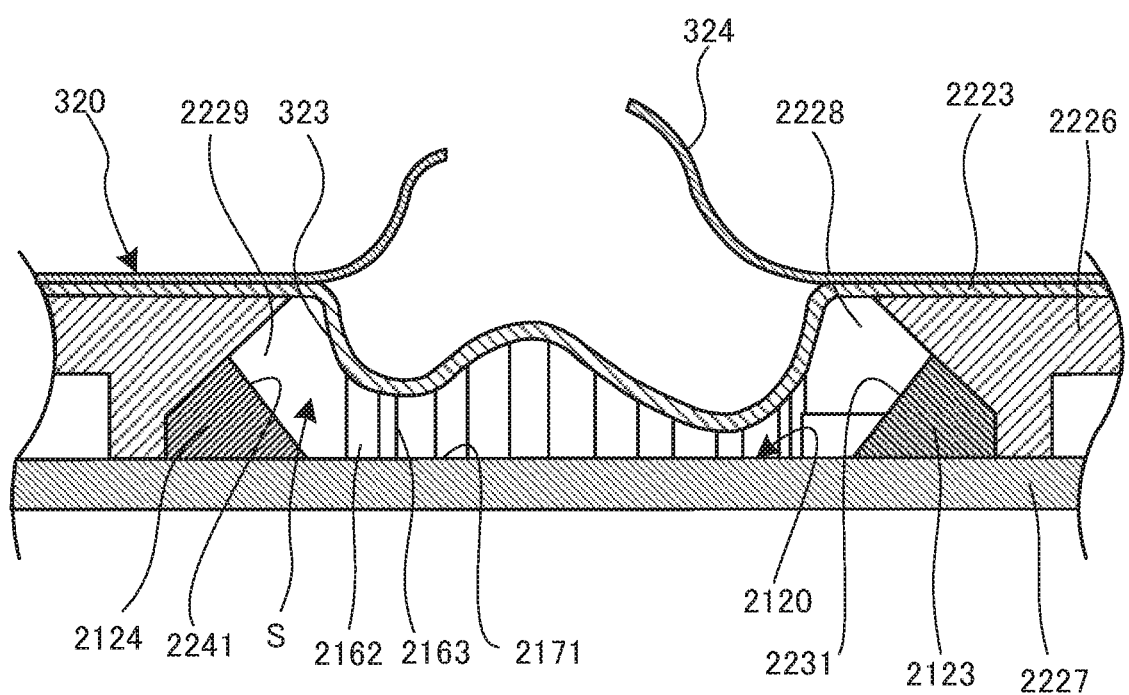
FIG. 25 is a sectional view, at the VIII-VIII position in FIG. 23, showing a state in which the contained object is pushed out from the containing portion.
Figure 26:
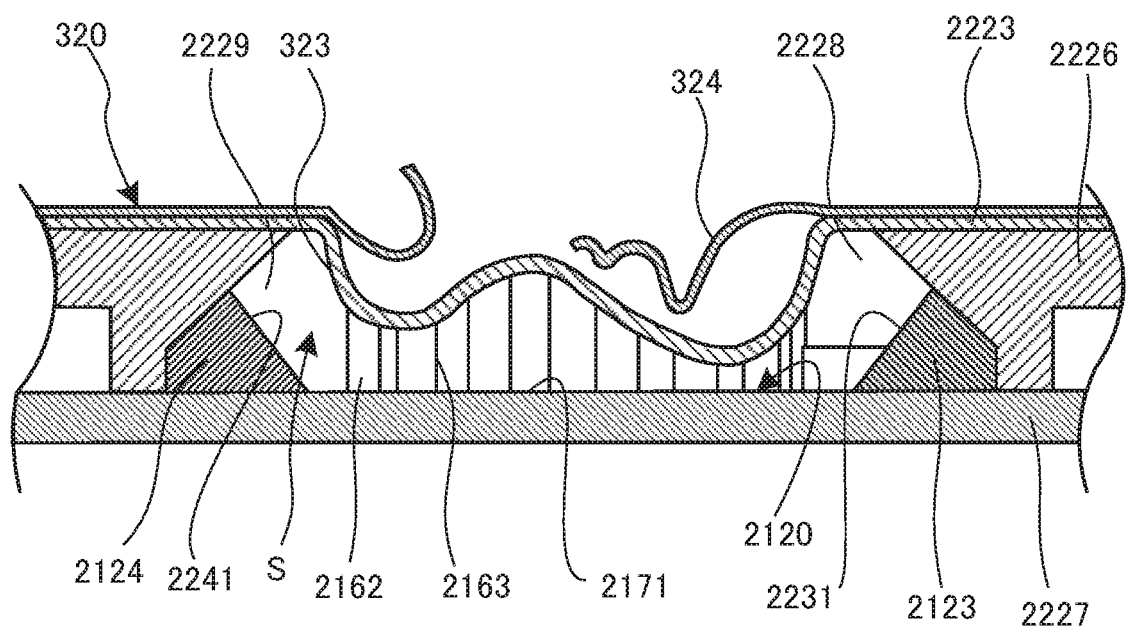
FIG. 26 is a sectional view, at the VIII-VIII position in FIG. 23, showing another state in which the contained object is pushed out from the containing portion.

The containing member 2122 includes, between the defining member main body 2226 and the board 2227 at positions adjacent to each inner wall surface 2120, an arrangement portion 2228 where the light source 2123 is arranged and an arrangement portion 2229 where the light receiver 2124 is arranged (see FIG. 22). The arrangement portions 2228 and 2229 each communicate with the containing space S, and are provided at positions facing each other in a radial direction when the circumferential surface portion 2162 is regarded as a columnar surface having a virtual axis 2260 as a central axis. The light source 2123 and the light receiver 2124 are arranged in the arrangement portions 2228 and 2229 in a state in which they are implemented on the board 2227.

Each of the plurality of circumferential surface portions 2162 has a cylindrical shape (columnar surface shape) surrounding the virtual axis 2260 extending in the thickness direction (predetermined direction) of the defining member main body 2226, and has at least one of a set of a plurality of convex portions and a set of a plurality of concave portions over the entire region in the circumferential direction. The circumferential surface portion 2162 according to this example embodiment includes a plurality of convex portions 2163 (see FIG. 23).

The plurality of convex portions 2163 extend in the same direction as that of the virtual axis 2260, and are arrayed in the circumferential direction of the circumferential surface portion 2162. Each convex portion 2163 has a triangular shape as a sectional shape orthogonal to the virtual axis 2260. That is, in the sectional shape of the circumferential surface portion 2162 orthogonal to the virtual axis 2260, convex and concave portions are alternately arrayed in a serrated shape (see FIG. 23). Each of the plurality of circumferential surface portions 2162 is a mirror finished surface. Each circumferential surface portion 2162 according to this example embodiment is a mirror finished surface obtained by silver deposition.

Note that the "columnar surface shape" as the shape of each circumferential surface portion 2162 includes a shape that looks like an almost circle such as an ellipse with a small oblateness or a polygon close to a circle, in addition to the shape obtained by repeating small concave and convex portions in the circumferential direction in the section orthogonal to the virtual axis 2260, as in this example embodiment.

With each circumferential surface portion 2162 having such shape, the light emitted from the light source 2123 is repeatedly reflected in various directions in the containing space S, and diffused.

The light source 2123 emits the light (light of a predetermined wavelength among wavelengths from the infrared region to the ultraviolet region) from the arrangement portion 2228 into the containing space S. This light source 2123 emits single-wavelength light. As described above, by narrowing the wavelength region of the light emitted to the containing space S, it becomes easy to remove the influence of disturbance light when the light is received by the light receiver 2124. The light source 2123 according to this example embodiment emits light of a wavelength in the infrared region. This light source 2123 emits the light from a predetermined position of the circumferential surface portion 2162 in a direction intersecting a normal direction at the predetermined position when regarding the circumferential surface portion 2162 as a columnar surface having the virtual axis 2260 as the central axis. More specifically, the light source 2123 according to this example embodiment is arranged so that a light emitting surface 2231 is in a posture inclined toward the opening (the opposite side of the board 2227) of the circumferential surface portion 2162 with respect to the virtual axis 2260 (see FIG. 22). The light source 2123 according to this example embodiment is an LED.

The light receiver 2124 is a so-called light receiving element, and outputs an electrical signal of a strength corresponding to the intensity of light received by a light receiving surface 2241. The light receiver 2124 according to this example embodiment receives the light that has been emitted from the light source 2123 into the containing space S, reflected repeatedly between the circumferential surface portion 2162 and the detection target object (in the example of this example embodiment, the containing portion 321 of the blister pack 320) contained in the containing space S, and diffused sufficiently. The light receiver 2124 is arranged at a position facing the light source 2123 in the circumferential surface portion 2162. The light receiver 2124 according to this example embodiment is arranged so that the light receiving surface 2241 is in a posture inclined toward the opening portion of the circumferential surface portion 2162 with respect to the virtual axis 2260 (see FIG. 22).

The detector 2105 is implemented on the board 2227. The detector 2105 detects the presence/absence of the contained object 330 in each containing portion 321 of the blister pack 320 in accordance with whether the intensity of the electrical signal received from each light receiver 2124 exceeds a predetermined threshold. When one inner wall surface 2120 and the light source 2123 and light receiver 2124 corresponding to the inner wall surface 2120 are set as one detection unit, the detector 2105 according to this example embodiment receives an electrical signal from each of the plurality of detection units while detecting the presence/absence of the contained object 330 in the containing portion 321 for each detection unit.

The detector 2105 outputs detection results to the external apparatus such as a smartphone using a radio wave. By installing predetermined medication management software in the smartphone or the like, the smartphone which has received the detection results can perform medication management. That is, it is possible to detect the containing portions 321 with no contained objects 330 among the plurality of containing portions 321 of the blister pack 320. Therefore, for example, whether a predetermined number of tablets are taken every day or whether a tablet is taken for every predetermined time can be managed.

Note that the external apparatus which receives output information from the detection apparatus 2100 is not limited to the smartphone, and may be a mobile terminal such as a PDA, a PC, a terminal dedicated for medication management, or the like. The external apparatus may be a server or the like provided at a location away from the use place of the detection apparatus 2100 and connected via a LAN, the Internet, or the like. That is, the external apparatus need only be an apparatus that uses the information about the presence/absence of the contained object 330 for each containing portion 321. The detection apparatus 2100 according to this example embodiment outputs the information about the presence/absence of the contained object 330 for each containing portion 321 to the external apparatus via wireless connection but may be configured to output the information about the presence/absence of the contained object 330 for each containing portion 321 to the external apparatus via wired connection.

The cover 202 is a plate-like member, and is attached to a long side of the rectangular plate-like main body 2102 to be pivotable about an axis along the long side. In this example embodiment, when the cover 202 is in the closed state (see FIG. 1), the cover 202 closes the opening of each containing space S (inner wall surface 2120) of the containing member 2122, and when the cover 202 is in the open state (see FIG. 2), the opening of each containing space S (inner wall surface 2120) is open. In the closed state, the cover 202 has a shape that covers, along one surface of the containing member 2122, almost the entire surface. Therefore, in the closed state, the cover 202 according to this example embodiment has a function of blocking light from the outside to the containing space S in addition to the function of pressing the blister pack 320 toward the opening peripheral portions 2223 of the inner wall surfaces 2120, that is, toward the containing member 2122.

Sixth Example Embodiment

A detection apparatus according to the sixth example embodiment of the present invention will be described next with reference to FIG. 27. The same reference numerals as in the fifth example embodiment denote the same components and a detailed description thereof will be omitted. Only different components will be described in detail.

Figure 27:
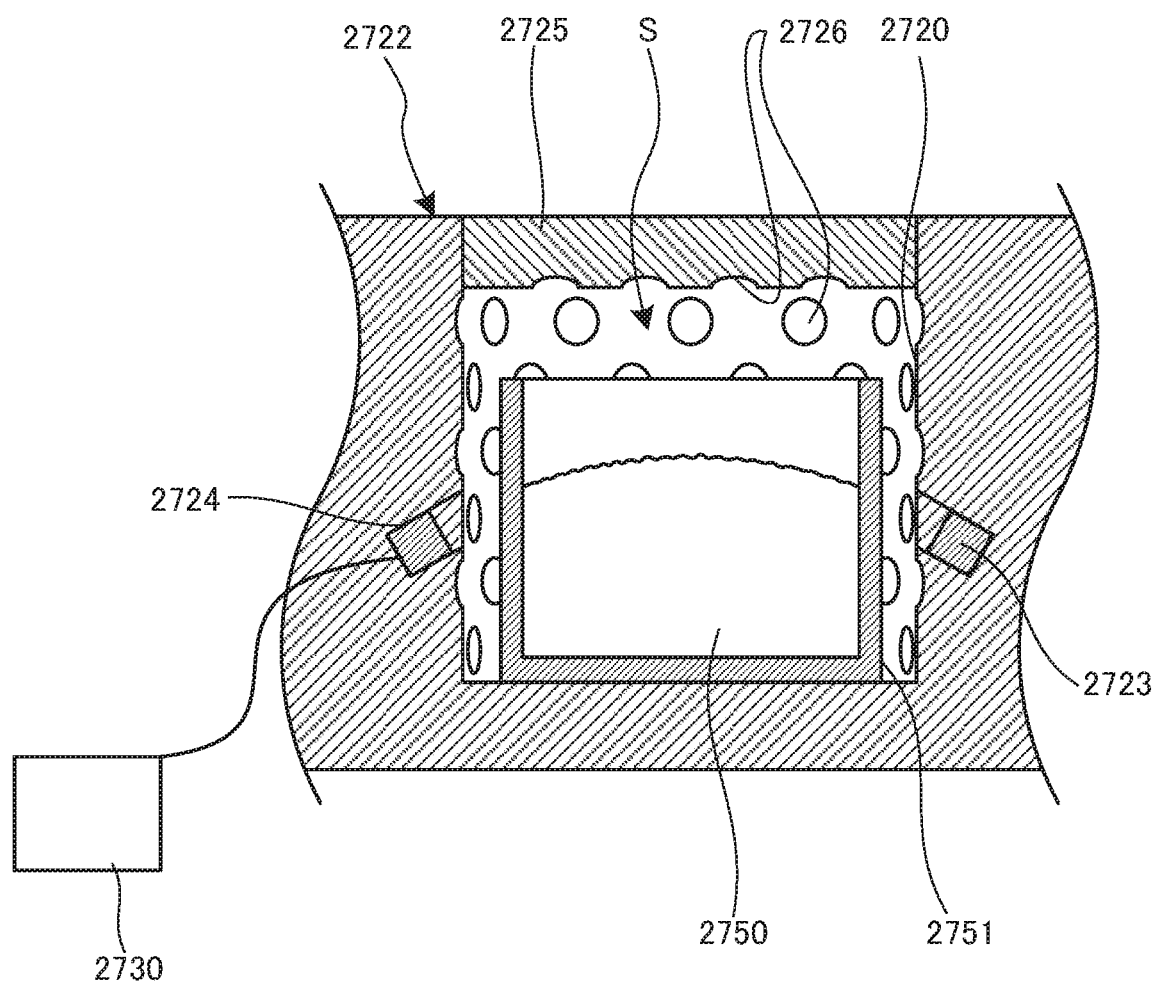
FIG. 27 shows a sectional view showing the containing space of a detection apparatus according to the sixth example embodiment of the present invention.

As shown in FIG. 27, the detection apparatus according to this example embodiment includes a containing space defining member 2722 having an inner wall surface 2720 for defining a containing space S in which a detection target object 2750 is contained, a light source 2723 that emits light to the containing space S, a diffuser that diffuses the light emitted from the light source 2723, and a light receiver 2724 that receives the light diffused in the containing space S, and also outputs an electrical signal of a strength corresponding to the light reception intensity. The detection apparatus according to this example embodiment includes a detector 2730 that detects the capacity of the detection target object by receiving the electrical signal from the light receiver 2724. In the detection apparatus according to this example embodiment, the diffuser includes the inner wall surface 2720.

The containing space defining member 2722 includes the inner wall surface 2720 for defining the closed containing space S. That is, although the containing member according to the fifth example embodiment forms the closed containing space S in cooperation with the blister pack, the containing space defining member 2722 according to this example embodiment forms (defines) the closed containing space S only by the inner wall surface 2720 of the containing space defining member 2722. In this containing space defining member 2722, when a lid 2725 is opened/closed, the detection target object 2750 is inserted/removed into/from the containing space S. The detection target object 2750 according to this example embodiment is, for example, a powder in a transparent container 2751.

The inner wall surface 2720 includes a plurality of concave portions 2726 (in the example shown in FIG. 27, dimple-shaped concave portions). The inner wall surface 2720 according to this example embodiment has the plurality of concave portion 2726 on the entire surface except for a surface on which the detection target object 2750 (more specifically, the container 2751) is arranged. The entire inner wall surface 2720 is a mirror finished surface. That is, the containing space S according to this example embodiment is surrounded by the mirror finished surface in all directions.

The detector 2730 includes, for example, a table for associating the strength of an electrical signal with the capacity of the detection target object 2750, and outputs, based on the table, the capacity of the detection target object 2750 corresponding to the strength of the electrical signal received from the light receiver 2724. This table is created by calculation, actual measurement, or the like based on the fact that the light reception intensity obtained when the light emitted from the light source 2723 is reflected in various directions and diffused sufficiently in a closed space (in the example of this example embodiment, the containing space S) and the light receiver 2724 receives the diffused light changes in accordance with the capacity of the closed space. More specifically, the table is created based on the fact that as the detection target object 2750 is larger (that is, a gap space between the detection target object 2750 and the inner wall surface 2720 is smaller), the number of times the light is reflected increases, the light attenuates, and thus the light reception intensity of the diffused light becomes lower while as the detection target object 2750 is smaller (that is, the gap space is larger), the number of times the light is reflected is suppressed, and thus the light reception intensity of the diffused light becomes higher. Note that the detector 2730 may obtain the capacity of the detection target object 2750 by calculation or the like based on the strength of the received electrical signal without using the table. That is, the detector 2730 need only be configured to derive the capacity of the detection target object 2750 based on the strength of the electrical signal received from the light receiver 2724.

The detector 2730 may be configured to output the detection result (the capacity of the detection target object) to the smartphone or the like using a radio wave or output the detection result to a screen provided in the detection apparatus or the like.

The detection apparatus with the above arrangement is used, as follows.

The lid 2725 of the containing space defining member 2722 is opened, the container 2751 containing the detection target object 2750 is placed in the containing space S, and then the lid 2725 is closed. When the detection apparatus detects the closing of the lid 2725 or a switch or the like is operated, the light source 2723 emits the light and the light receiver 2724 receives the light that has been repeatedly reflected in the containing space S and diffused sufficiently. The light receiver 2724 outputs an electrical signal of a strength corresponding to the light reception intensity to the detector 2730. The detector 2730 obtains (detects) the capacity of the detection target object 2750 based on the table and the strength of the electrical signal received from the light receiver 2724, and outputs a detection result using a radio wave.

In the above detection apparatus, if the light emitted into the containing space S is diffused in the containing space S, the light reception intensity (light amount) at the light receiver 2724 changes in accordance with the capacity of a space (the gap space between the inner wall surface 2720 and the surface of the detection target object 2750) except for the detection target object 2750 in the containing space S. Therefore, in the detection apparatus according to this example embodiment, when the light source 2723 emits the light into the containing space S, the light receiver 2724 which has received the light repeatedly reflected by the detection target object 2750 and the inner wall surface 2720 and sufficiently diffused outputs an electrical signal of a strength corresponding to the capacity of the detection target object 2750, and the detector 2730 derives the capacity of the detection target object 2750 based on the electrical signal.

In the detection apparatus according to this example embodiment, the mirror finished inner wall surface 2720 includes the plurality of concave portions 2726 to form the diffuser. In this arrangement, the light from the light source 2723 or the light reflected by the detection target object 2750 and the like is further reflected (diffused) in various directions by the plurality of concave portions 2726 of the inner wall surface 2720. Therefore, the light emitted from the light source 2723 into the containing space S is further diffused in the gap space (the space between the inner wall surface 2720 and the surface of the detection target object 2750), and thus the strength of the electrical signal output from the light receiver 2724 corresponds to the size of the gap space accurately. As a result, the capacity of the detection target object 2750 is derived accurately based on the electrical signal output from the light receiver 2724.

Note that the detailed shape of each convex or concave portion of the inner wall surface 2720 is not limited. For example, the inner wall surface 2720 may have the convex and concave portions, and each of the convex and concave portions may have a conical shape, a columnar shape, or the like. That is, each of the convex and concave portions need only have a shape that irregularly reflects the light in various directions in the containing space S.

According to each of the fifth and sixth example embodiments, the entire inner wall surface 2120 need not be a mirror finished surface. That is, part of the inner wall surface 2120 may be a mirror finished surface. As long as an arrangement (wall surface) in which the light is reflected efficiently is adopted, the inner wall surface 2120 need not be a mirror finished surface.

The detailed direction in which the light source 2123 emits the light is not limited. The light source 2123 according to the fifth example embodiment emits the light from the predetermined position of the circumferential surface portion 2162 in the direction intersecting the normal direction at the predetermined position when regarding the circumferential surface portion 2162 as the columnar surface having the virtual axis 2260 as the central axis but may emit the light in the normal direction. That is, the light source 2123 need only be able to emit the light in a direction in which the light is repeatedly reflected between the inner wall surface 2120 and the detection target object (the contained object in the fifth example embodiment or the detection target object 2750 in the sixth example embodiment).

Furthermore, the light emitted by the light source 2123 or 2723 is not limited to light of a wavelength in the infrared region. The light may have a wavelength in the ultraviolet region or visible light region. That is, the light emitted by the light source 2123 or 2723 is light of a wavelength in one of the wavelength regions including the infrared, visible light, and ultraviolet regions.

Note that as for infrared light (light of a wavelength in the infrared region), detection of the capacity of the detection target object or detection of the presence/absence of the contained object is performed accurately by emitting the infrared light continuously. On the other hand, as for ultraviolet light (light of a wavelength in the ultraviolet region), the pulsed light is preferably emitted. Since external light that may enter the containing space S as disturbance light includes much ultraviolet light (light of a wavelength in the ultraviolet region), this is done to make it easy to remove the influence of the disturbance light from the electrical signal output from the light receiver 2124 or 2724. That is, when the light source 2123 or 2723 emits pulse light (pulsed ultraviolet light) having a constant intensity, the intensity of disturbance light (more specifically, ultraviolet light included in disturbance light) is obtained from the light reception intensity (the strength of the electrical signal output from the light receiver 2124 or 2724) at the light receiver 2124 or 2724 while the light source 2123 or 2723 emits the light and the light reception intensity (the strength of the electrical signal output from the light receiver 2124 or 2724) at the light receiver 2124 or 2724 while the light source 2123 or 2723 emits no light. Thus, it is possible to readily remove the influence of the disturbance light from the electrical signal output from the light receiver 2124 or 2724.

Seventh Example Embodiment

A detection apparatus according to the seventh example embodiment of the present invention will be described with reference to FIG. 28. The same reference numerals as in the fifth example embodiment denote the same components and a detailed description thereof will be omitted. Only different components will be described in detail.

In the detection apparatus according to each of the fifth and sixth example embodiments, one light source 2123 or 2723 and one light receiver 2124 or 2724 are arranged in one detection unit. The present invention, however, is not limited to this. At least one light source and at least one light receiver are arranged in one detection unit.

Figure 28:
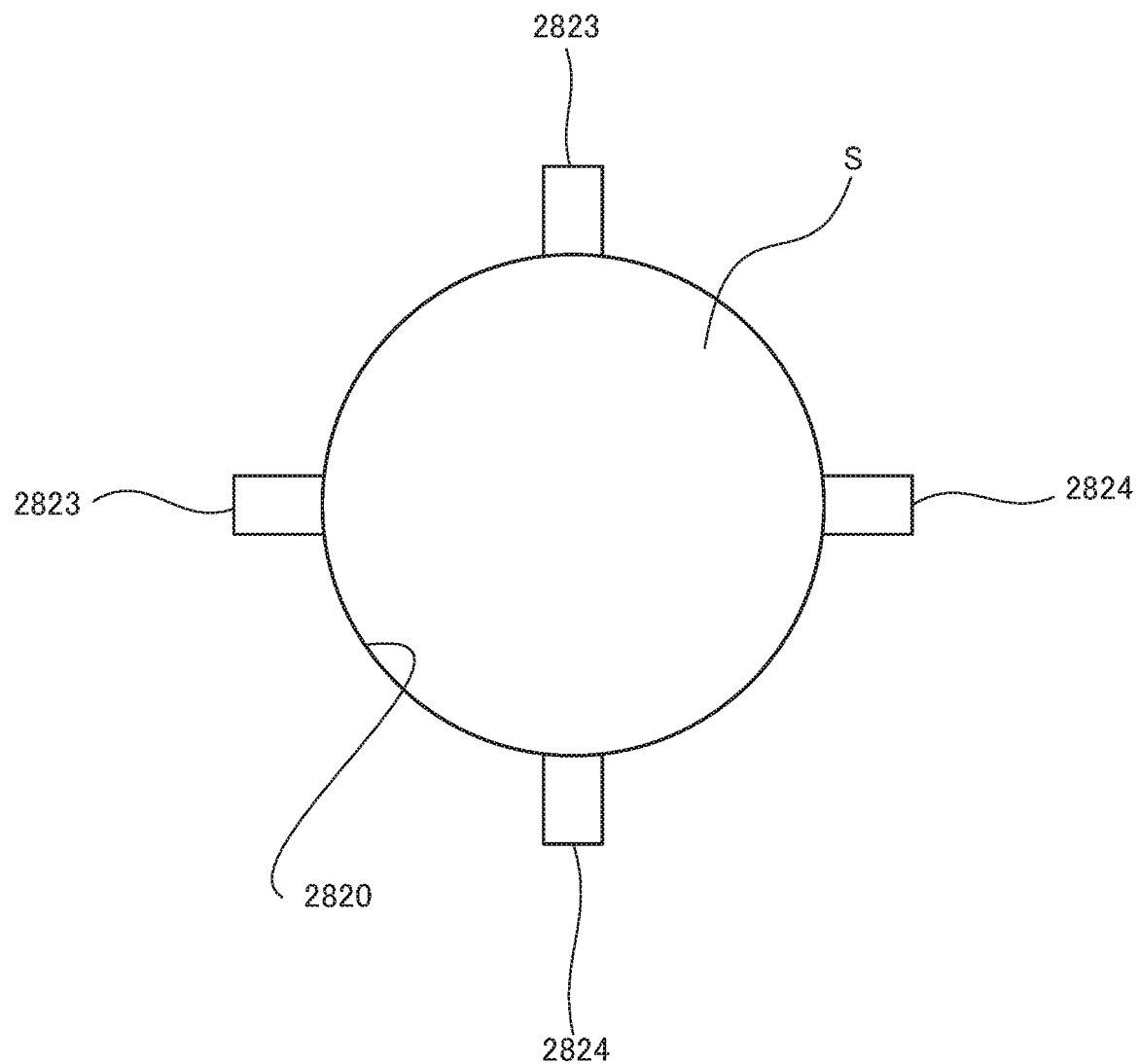
FIG. 28 is a view for explaining a detection apparatus according to the seventh example embodiment of the present invention.

In this case, for example, in the example shown in FIG. 28, an arrangement can be adopted, in which after one of two light sources 2823 arranged at different positions emits light, and a light receiver 2824 facing the one light source 2823 via a containing space S receives scattered light, while one light source 2823 stops emitting light, the other light source 2823 emits light, and the light receiver 2824 facing the other light source 2823 via the containing space S receives scattered light. That is, one light source 2823 and one light receiver 2824 that receives light which has been emitted from the light source 2823 and scattered may be paired, and a plurality of pairs may be arranged. Alternatively, the plurality of light sources 2823 may emit light beams simultaneously, and one light receiver 2824 may receive scattered light, or one light source 2823 emits light, and the plurality of light receivers 2824 may receive scattered light beams simultaneously. The plurality of light sources 2823 may emit light beams simultaneously, and the plurality of light receivers 2824 may receive scattered light beams simultaneously. In these cases, not all the light sources 2823 need to emit light beams in the same wavelength region.

In the inner wall surface 2120 according to each of the fifth and sixth example embodiments, at least one of a set of a plurality of convex portions and a set of a plurality of concave portions are arranged. The present invention, however, is not limited to this. An inner wall surface 2820 according to this example embodiment may be spherical or columnar without local unevenness. The inner wall surface 2820 may be a regular polyhedron or the like. In these cases, if the inner wall surface 2820 is formed by a mirror finished surface, and the light source 2823 emits the light from a predetermined position of the inner wall surface 2820 in a direction intersecting a radial direction (a direction toward the center of the sphere, the central axis of the cylinder, or the center of the regular polyhedron), the emitted light is readily, irregularly reflected (repeatedly reflected in various directions), and thus diffused sufficiently.

The diffuser according to each of the fifth to seventh example embodiments includes the inner wall surface. The present invention, however, is not limited to this. The diffuser is formed by a plurality of reflecting plates and the like arranged in the containing space S, and may be configured to reflect, in various directions, the light emitted from the light source and diffuse it. Furthermore, the diffuser may be formed by the inner wall surface, the reflecting plates arranged in the containing space S, and the like.

The light emitting surface of the light source is not limited to the plane. For example, the light source may be configured to emit light in various directions by having a convex portion as a light emitting surface. In this arrangement, the light emitted from the light source is readily further diffused in the containing space S.

Furthermore, the light receiving surface of the light receiver is not limited to the plane. For example, the light receiver may be configured to have a parabolic light receiving surface. In this arrangement, the diffused light (light traveling in various directions) in the containing space S is readily received, thereby readily ensuring the light reception intensity on the light receiving surface.

Although the detection apparatus according to the fifth example embodiment outputs the information about the presence/absence of the contained object for each containing portion to the external apparatus, the present invention is not limited to this. The detection apparatus may include a display unit such as a liquid crystal display, a plasma display, or an organic EL display, and may be configured to display the information about the presence/absence of the contained object or an image based on the information on the display unit. Alternatively, the detection apparatus may be configured to output (print out), as a character, an image, or the like, the information about the presence/absence of the contained object onto a sheet surface.

In the detection apparatus of the blister pack according to the fifth example embodiment, the containing portions of the blister pack are transparent. The present invention, however, is not limited to this. The containing portions may be opaque.

Overview of Fifth to Seventh Example Embodiments

As described above, these example embodiments are based on the fact that when a light receiving element or the like (light receiver) receives light diffused sufficiently by reflecting, in various directions, light emitted from a light source in a closed space, the light reception intensity changes in accordance with the capacity of the closed space. That is, if a detection target object is arranged in the closed space and the light emitted from the light source in the closed space is reflected in various directions and diffused sufficiently, the light reception intensity when the light receiver receives the diffused light corresponds to the capacity (in other words, the capacity of a gap space between an inner wall surface for defining the closed space and the surface of the detection target object) obtained by excluding the capacity of the detection target object from the capacity of the closed space. More specifically, as the detection target object is larger (that is, the gap space is smaller), the number of times the light is reflected increases, the light attenuates, and thus the light reception intensity of the diffused light becomes lower. On the other hand, as the detection target object is smaller (that is, the gap space is larger), the number of times the light is reflected is suppressed, and thus the light reception intensity of the diffused light becomes higher.

Based on these findings, attention is paid to the correspondence between the capacity of the gap space and the light reception intensity at the light receiver of the diffused light when the light is diffused sufficiently in the closed space, thereby implementing the detection apparatus according to each of the fifth to seventh example embodiments.

The detection apparatus according to each of the fifth to seventh example embodiments includes the inner wall surface that defines the containing space in which the detection target object is contained, the light source that emits the light into the containing space, the diffuser that diffuses the light emitted from the light source, and the light receiver that receives the diffused light in the containing space, and also outputs the electrical signal of the strength corresponding to the light reception intensity.

If the light emitted into the containing space is diffused in the containing space, the light reception intensity (light amount) of the diffused light at the light receiver changes in accordance with the capacity of the space (the gap space between the inner wall surface and the surface of the detection target object) except for the detection target object in the containing space. Therefore, in the above-described arrangement, when the light emitted from the light source is diffused by the diffuser in the containing space, the light receiver which has received the diffused light outputs the electrical signal of the strength corresponding to the capacity of the detection target object. Based on the electrical signal output from the light receiver, the capacity of the detection target object can be detected.

In the detection apparatus according to each of the fifth to seventh example embodiments, the inner wall surface may include at least one of a convex portion and a concave portion, and the diffuser may include the inner wall surface.

According to this arrangement, since the light from the light source or the light reflected by the detection target object or the like is further reflected (diffused) in various directions by at least one of the convex and concave portions of the inner wall surface, the light emitted from the light source into the containing space is further diffused in the gap space, and thus the strength of the electrical signal output from the light receiver which has received the diffused light corresponds to the size of the gap space more accurately.

Therefore, based on the electrical signal output from the light receiver, the capacity of the detection target object can be detected more accurately.

In the detection apparatus according to each of the fifth to seventh example embodiments, the inner wall surface may include at least one of a set of a plurality of convex portions and a set of a plurality of concave portions, and include the cylindrical circumferential surface portion surrounding the virtual axis extending in the predetermined direction, and at least one of the set of the convex portions and the set of the concave portions may be arranged over the entire region in the circumferential direction of the circumferential surface portion.

According to this arrangement, since the light is reflected (diffused) in various directions in the entire region in the circumferential direction of the circumferential surface portion, the light emitted from the light source is diffused sufficiently in the containing space, and thus the strength of the electrical signal output from the light receiver which has received the diffused light corresponds to the size of the gap space more accurately.

In this case, at least one of the set of the convex portions and the set of the concave portions may extend in the same direction as that of the virtual axis.

With the simple arrangement including the convex portions or concave portions extending in one direction (the direction of the virtual axis), it is possible to reflect the light in various directions in the entire region in the circumferential direction of the circumferential surface portion.

In the detection apparatus according to each of the fifth to seventh example embodiments, the light source may emit the light from the predetermined position of the circumferential surface portion in the direction intersecting the normal direction at the predetermined position of the circumferential surface portion.

According to this arrangement, if there is the detection target object near the predetermined position of the circumferential surface portion, the amount of light that is reflected by the detection target object to return to the light source (a light emitting surface or the like) is suppressed, as compared to a case in which the light source emits the light in the normal direction at the predetermined position. This suppresses a decrease in diffused light in the gap space, which is necessary to detect the capacity of the detection target object.

In the detection apparatus according to each of the fifth to seventh example embodiments, the circumferential surface portion may have the columnar surface shape, and the light source and the light receiver may be arranged, in the circumferential surface portion, at the positions facing each other in the radial direction of the circumferential surface portion.

According to this arrangement, since the light receiver is arranged at a position farthest from the light source in the circumferential direction of the circumferential surface portion, the light which is sufficiently, repeatedly reflected and diffused is received, as compared to a case in which the light receiver is arranged near the light source. Thus, the strength of the electrical signal output from the light receiver corresponds to the size of the gap space more accurately.

In the detection apparatus according to each of the fifth to seventh example embodiments, in the inner wall surface, at least the circumferential surface portion may be a mirror finished surface.

According to this arrangement, attenuation of the light caused by reflection is suppressed over the entire region in the circumferential direction of the circumferential surface portion, and the light reception intensity at the light receiver increases. Therefore, the strength of the electrical signal output from the light receiver corresponds to the size of the gap space more accurately.

The detection apparatus according to each of the fifth to seventh example embodiments includes the inner wall surface that defines the containing space in which the detection target object is contained, the light source that emits the light into the containing space, and the light receiver that receives the diffused light in the containing space, and also outputs the electrical signal of the strength corresponding to the light reception intensity, wherein the inner wall surface is a mirror finished surface, and includes the cylindrical circumferential surface portion surrounding the virtual axis extending in the predetermined direction, the light source emits the light from the predetermined position of the circumferential surface portion in the direction intersecting the normal direction at the predetermined position of the circumferential surface portion, and the light receiver is arranged at the position facing the light source in the circumferential surface portion in the radial direction of the circumferential surface portion.

According to this arrangement, since the light emitted from the light source is repeatedly reflected by the detection target object or the inner wall surface and diffused sufficiently, and then reaches the light receiver, the strength of the electrical signal output from the light receiver corresponds to the size of the gap space accurately.

In the detection apparatus according to each of the fifth to seventh example embodiments, the light source preferably emits light of a wavelength in the infrared region.

External light that may enter the containing space as disturbance light includes much light of a short wavelength (for example, light of a wavelength in the ultraviolet region). Therefore, the influence of the disturbance light at the time of detection can be suppressed by using, for detection of the detection target object, the light of a wavelength in the infrared region where the wavelength is long.

The contained object detection apparatus of the blister pack according to each of the fifth to seventh example embodiments includes one of the above-described detection apparatuses, and the detector that detects the presence/absence of the contained object in the containing portion of the blister pack by receiving the electrical signal from the detection apparatus, wherein the inner wall surface has the opening, and has the shape such that the containing space becomes a closed space when the opening peripheral portion of the inner wall surface abuts against the periphery of the containing portion of the blister pack in a state in which the containing portion as the detection target object of the detection apparatus is inserted from the opening into the containing space, and the detection unit detects the presence/absence of the contained object in the blister pack based on the strength of the electrical signal.

According to this arrangement, even if there is part (for example, the containing portion in a crushed state after the contained object is pushed out, or a sheet such as a mount or aluminum foil that closed the opening of the containing portion) of the blister pack between the light source and the light receiver, it is possible to detect the presence/absence of the contained object in the containing portion by using the detection apparatus capable of sensing the capacity of the detection target object in the containing space by the diffused light. More specifically, when an arrangement is adopted, in which an appropriate threshold is set for the capacity of the detection target object in the contained space detected using the diffused light, that is, the strength of the electrical signal output from the light receiver, and the presence/absence of the contained object in the containing portion of the blister pack is detected in accordance with whether the strength of the electrical signal received from the light receiver by the detector exceeds the threshold, even if there is an object (part of the blister pack) between the light source and the light receiver that receives the light emitted from the light source, that is, on the trajectory of the light traveling directly from the light source to the light receiver, it is possible to detect the presence/absence of the contained object in the containing portion.

In the contained object detection apparatus of the blister pack, when the inner wall surface, the light source, and the light receiver are set as one detection unit, the detection apparatus may include a plurality of detection units, the plurality of detection units may be arranged at positions corresponding to the plurality of containing portions of the blister pack, and the detector may receive the electrical signal from each of the plurality of detection units, and also detect the presence/absence of the contained object for each detection unit.

According to this arrangement, it is possible to detect the presence/absence of the contained object for each of the plurality of containing portions of the blister pack.

The contained object detection apparatus of the blister pack may include a pressing portion that presses the blister pack toward the opening peripheral portion of the inner wall surface in a state in which the containing portion of the blister pack is contained in the containing space.

According to this arrangement, when detecting the presence/absence of the contained object in the containing portion, the pressing portion presses the blister pack, and the opening peripheral portion of the inner wall surface and the periphery of the containing portion of the blister pack are in tight contact with other, that is, it is difficult to generate a gap between the opening peripheral portion and the periphery of the containing portion. This prevents external light (disturbance light) from entering the containing space.

The containing member according to each of the fifth to seventh example embodiments includes the inner wall surface that defines the containing space in which the detection target object is contained, a first arrangement portion in which the light source that emits light into the containing space can be arranged, and a second arrangement portion in which the light receiver that receives the light in the containing space can be arranged, wherein the inner wall surface is a mirror finished surface and includes at least one of a convex portion and a concave portion.

According to this arrangement, by arranging the light source and the light receiver in the first arrangement portion and the second arrangement portion, respectively, it is possible to obtain the detection apparatus capable of detecting the capacity of the detection target object by sensing performed when the light receiver receives the light emitted from the light source.

Eighth Example Embodiment

Figure 29:
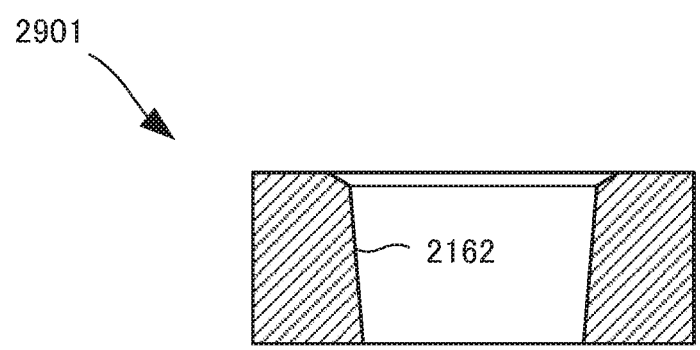
FIG. 29 is a view for explaining a detection apparatus according to the eighth example embodiment of the present invention.

A detection apparatus according to the eighth example embodiment of the present invention will be described next with reference to FIG. 29. FIG. 29 is a view for explaining a circumferential surface portion 2162 of the detection apparatus according to this example embodiment. The circumferential surface portion 2162 according to this example embodiment is different from the above-described fifth example embodiment in that a tapered portion and a C surface are included. The remaining components and operations are the same as those in the fifth example embodiment. Hence, the same reference numerals denote the same components and operations, and a detailed description thereof will be omitted.

Figure 30:
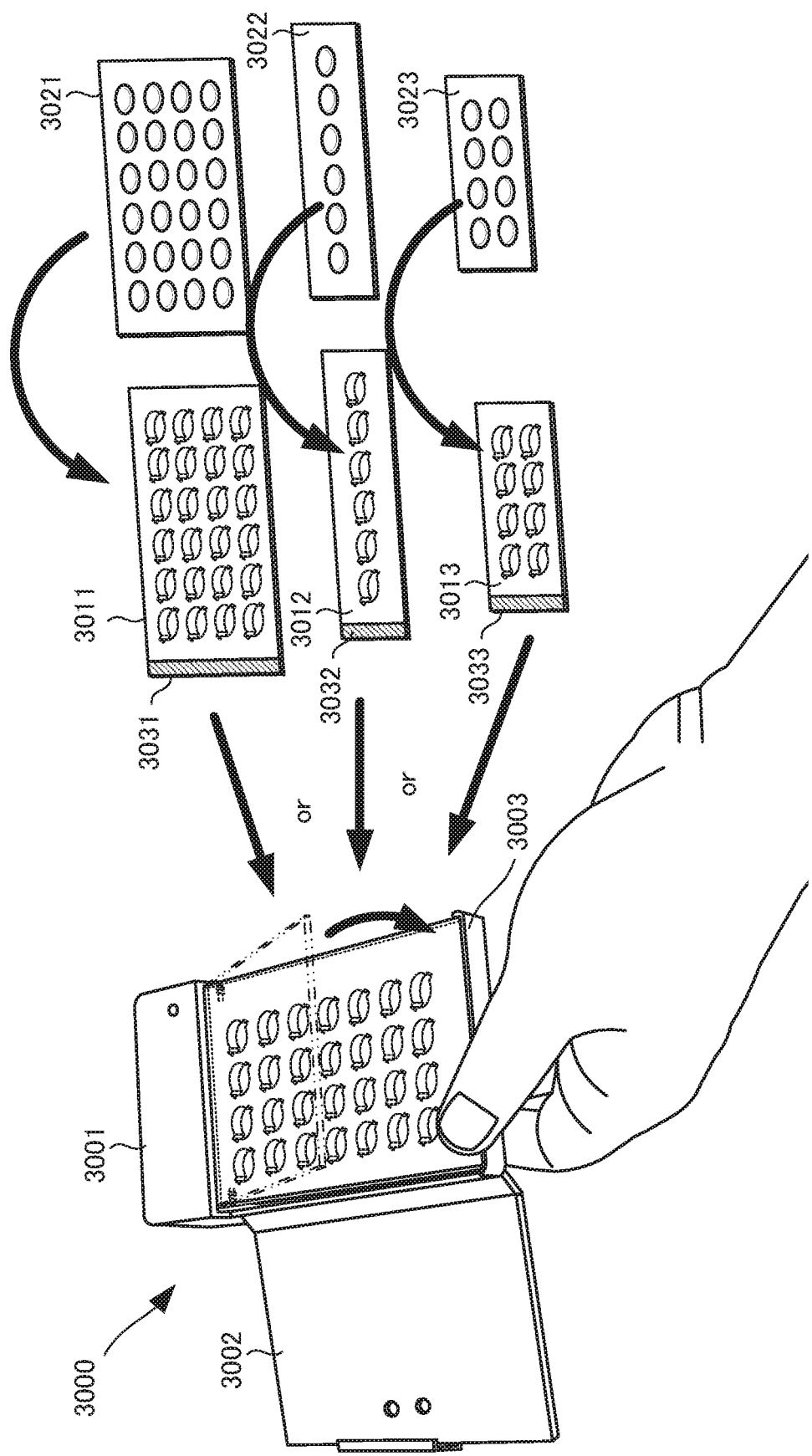
FIG. 30 is a view for explaining a detection apparatus according to the ninth example embodiment of the present invention.

Referring to FIG. 29, as indicated by a section 2901, the circumferential surface portion 2162 is provided with the tapered portion, and chamfered at the inlet of a blister pack. This makes it possible to readily insert the blister pack, and arrange it at a deep position reliably Ninth Example Embodiment A detection apparatus according to the ninth example embodiment of the present invention will be described next with reference to FIG. 30. FIG. 30 is a view for explaining the arrangement of the detection apparatus according to this example embodiment. The detection apparatus according to this example embodiment is different from the above-described second example embodiment in that a plurality of arrangement units 3011 to 3013 for arranging a plurality of types of blister packs 3021 to 3023 are connected replaceably. The remaining components and operations are the same as those in the second example embodiment. Hence, the same reference numerals denote the same components and operations, and a detailed description thereof will be omitted.

Each of the arrangement units 3011 to 3013 includes a porous plate and a board to which LEDs and sensors are attached, and includes none of a microcontroller 302, button battery 523, and communication module 524, all of which are contained in a microcomputer cover 504.

At the time of use, a terminal 3031, 3032, or 3033 provided in one of the arrangement units 3011 to 3013 is inserted into a main body 3001 and set in a housing 3003. This connects the LEDs and sensors provided in one of the arrangement units 3011 to 3013 to the microcontroller (not shown) of the main body 3001, thereby performing contained object detection processing.

According to this example embodiment, one detection apparatus can detect contained objects in various types of blister packs. If an arrangement unit corresponding to the type of a blister pack is selected and set in the detection apparatus in a pharmacy, it is possible to readily manage taking of a plurality of kinds of tablets and capsules using the common main body.

10th Example Embodiment

Figure 31:
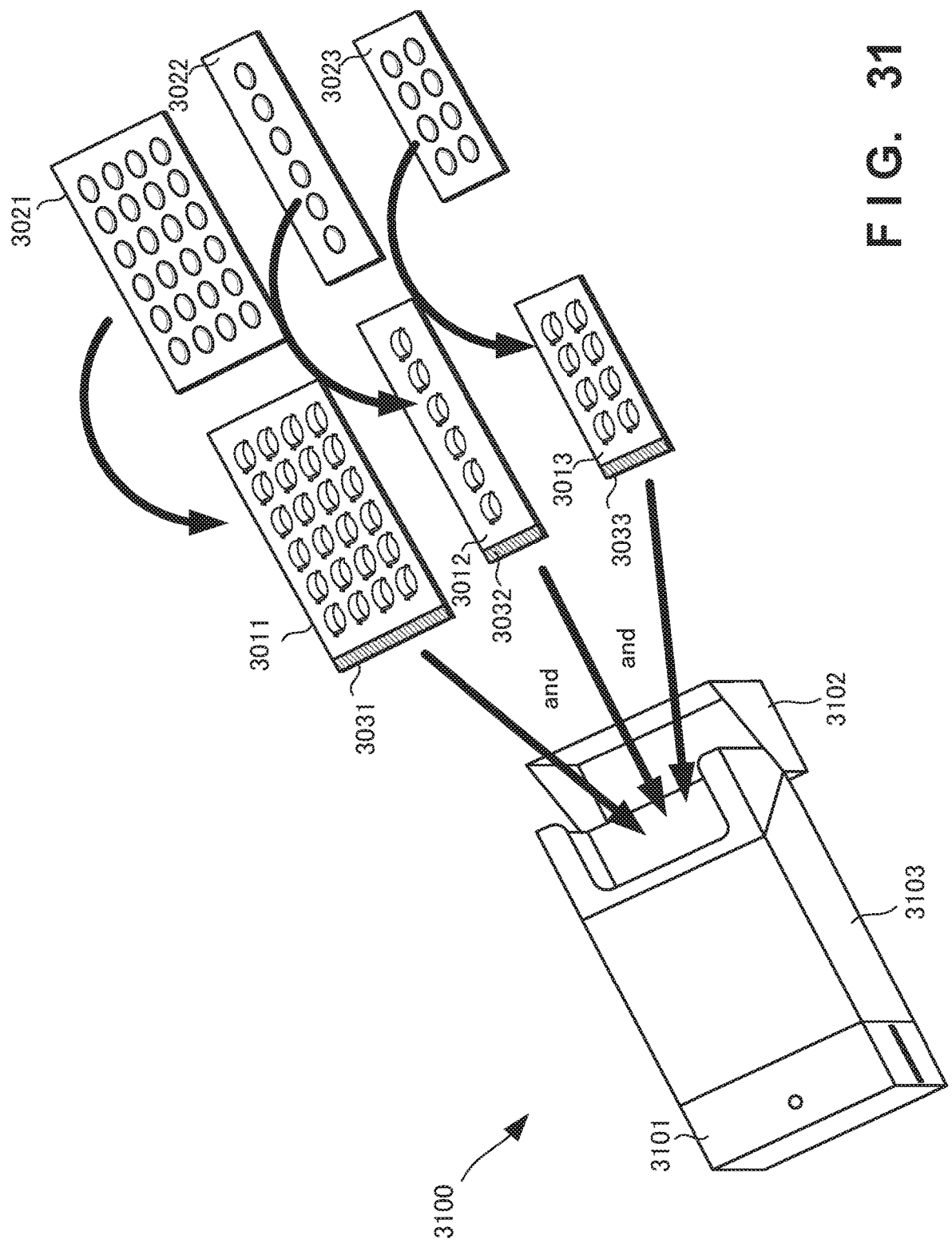
FIG. 31 is a view for explaining a detection apparatus according to the 10th example embodiment of the present invention.
Figure 32:
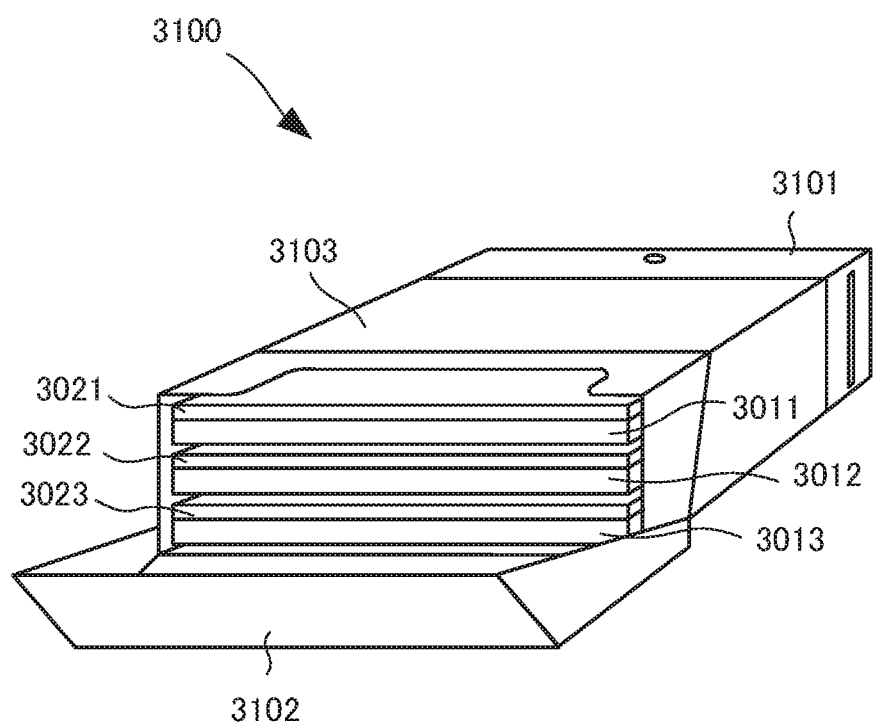
FIG. 32 is a view for explaining the detection apparatus according to the 10th example embodiment of the present invention.

A detection apparatus according to the 10th example embodiment of the present invention will be described next with reference to FIGS. 31 and 32. FIG. 31 is a view for explaining an arrangement at the time of use of a detection apparatus 3100 according to this example embodiment, and FIG. 32 is a view showing the internal state of the detection apparatus 3100. The detection apparatus 3100 according to this example embodiment is different from the above-described ninth example embodiment in that a box-shaped housing 3103 is included and a plurality of arrangement units 3011 to 3013 can be stacked (in three stages as an example) and connected at the same time. The remaining components and operations are the same as those in the ninth example embodiment. Hence, the same reference numerals denote the same components and operations, and a detailed description thereof will be omitted.

A main body 3101 includes a plurality of stages of connectors (not shown), and is configured to connect the plurality of stacked arrangement units 3011 to 3013 at the same time. If a plurality of types of blister packs 3021 to 3023 are arranged and attached to the arrangement units 3011 to 3013, respectively, and connected to the main body 3101, and the lid 3102 is then closed, detection of all contained objects in the blister packs 3021 to 3023 starts.

According to this example embodiment, one detection apparatus can detect the contained objects of the various types of blister packs simultaneously. For example, it is possible to readily manage taking of a plurality of kinds of tablets, capsules, and the like using the common main body, thereby implementing flexibility of the apparatus.

Other Example Embodiments

While the invention has been particularly shown and described with reference to example embodiments thereof, the invention is not limited to these example embodiments. It will be understood by those of ordinary skill in the art that various changes in form and details may be made therein without departing from the spirit and scope of the present invention as defined by the claims.

The present invention is applicable to a system including a plurality of devices or a single apparatus.

The invention claimed is:

1. A detection apparatus for detecting whether a contained object exists in a blister pack including a plurality of containing portions and a sheet covering the plurality of containing portions, the apparatus comprising:
a plate on which the blister pack is arranged;
a cover having a function of pressing the blister pack toward said plate in a closed state;
a plurality of light sources that emit light beams to the plurality of containing portions of the blister pack arranged on said plate;
a plurality of sensors that receive the light beams emitted from said light sources and reflected by the sheet or the cover, and also output electrical signals corresponding to light reception intensities; and
a detector that detects the presence/absence of contained objects in the respective containing portions based on the electrical signals output from said plurality of sensors;
wherein light reflected by the sheet or the cover is received by the plurality of sensors so that the detector correctly detects the presence/absence of contained objects in the respective containing portions thereby avoiding a false reading.

2. The detection apparatus according to claim 1, wherein an inner surface of said cover has a color with a high reflectance.

3. The detection apparatus according to claim 1, further comprising an opening/closing detector of said cover,
wherein said opening/closing detector causes said light sources to emit the light beams using, as a trigger, detection of closing of said cover, and causes said sensors to receive the light beams, thereby detecting the presence/absence of the contained objects in the respective containing portions.

4. The detection apparatus according to claim 1, wherein said light sources emit the light beams in a direction of said cover, and said sensors receive the light beams from the direction of said cover.

5. The detection apparatus according to claim 1, wherein said plate includes concave portions, the number, positions, and sizes of which correspond to the containing portions, to insert the respective containing portions of the blister pack,
said light sources and said sensors are arranged in said concave portions, respectively, and
said light sources emit the light beams toward directions other than directions of said sensors.

6. The detection apparatus according to claim 5, wherein bottom surfaces of said concave portions have a color with a low light reflectance.

7. A detection method of detecting whether a contained object exists in a blister pack including a plurality of containing portions and a sheet covering the plurality of containing portions, the method comprising:
pressing, using a cover, the blister pack in a closed state toward a plate on which the blister pack is arranged; and
detecting, using a plurality of light sources that emit light beams to the plurality of containing portions of the blister pack and a plurality of sensors that receive the light beams emitted from the light sources and reflected by the sheet or the cover, and also output electrical signals corresponding to light reception intensities, the presence/absence of contained objects in the respective containing portions based on the electrical signals output from the plurality of sensors;
wherein light reflected by the sheet or the cover is received by the plurality of sensors so that said detecting step correctly detects the presence/absence of contained objects in the respective containing portions thereby avoiding a false reading.

8. A medication management system for managing a timing at which a medicine is taken out from a blister pack including a plurality of containing portions and a sheet covering the plurality of containing portions, the system comprising:
a plate on which the blister pack is arranged;
a cover having a function of pressing the blister pack toward said plate in a closed state;
a plurality of light sources that emit light beams to the plurality of containing portions of the blister pack arranged on said plate;
a plurality of sensors that receive the light beams emitted from said light sources and reflected by the sheet or the cover, and also output electrical signals corresponding to light reception intensities;
a detector that detects the presence/absence of contained objects in the respective containing portions based on the electrical signals output from said plurality of sensors; and
a display unit that displays detection results by said detector;
wherein light reflected by the sheet or the cover is received by the plurality of sensors so that the detector correctly detects the presence/absence of contained objects in the respective containing portions thereby avoiding a false reading.

* * * * *